(12) United States Patent
Skold

(10) Patent No.: US 8,029,810 B2
(45) Date of Patent: Oct. 4, 2011

(54) WATER-BASED DELIVERY SYSTEMS

(75) Inventor: Thomas Skold, Norrtalje (SE)

(73) Assignee: Thomas Skold, Norrtalje (SE)

( * ) Notice: Subject to any disclaimer, the term of this patent is extended or adjusted under 35 U.S.C. 154(b) by 297 days.

(21) Appl. No.: 12/290,455

(22) Filed: Oct. 30, 2008

(65) Prior Publication Data
US 2009/0226491 A1 Sep. 10, 2009

Related U.S. Application Data

(63) Continuation of application No. 10/957,320, filed on Sep. 30, 2004, now abandoned, which is a continuation-in-part of application No. PCT/US03/07752, filed on Mar. 13, 2003, and a continuation-in-part of application No. 10/388,371, filed on Mar. 13, 2003, now abandoned.

(60) Provisional application No. 60/365,059, filed on Mar. 13, 2002.

(51) Int. Cl.
A61K 9/00 (2006.01)
A61K 31/74 (2006.01)
A61K 47/00 (2006.01)

(52) U.S. Cl. ............ 424/400; 424/78.02; 514/784

(58) Field of Classification Search .......... 424/400, 424/78.02; 514/784
See application file for complete search history.

(56) References Cited

U.S. PATENT DOCUMENTS

| | | | |
|---|---|---|---|
| 4,508,703 A | 4/1985 | Redziniak et al. | |
| 4,610,868 A | 9/1986 | Fountain et al. | |
| 5,196,190 A | 3/1993 | Nangia et al. | |
| 5,206,020 A | 4/1993 | Critchley et al. | |
| 5,298,246 A | 3/1994 | Yano et al. | |
| 5,320,906 A | 6/1994 | Eley et al. | |
| 5,468,475 A | 11/1995 | Shaku et al. | |
| 5,534,499 A | 7/1996 | Ansell | |
| 5,593,622 A | 1/1997 | Yoshioka et al. | |
| 5,628,936 A | 5/1997 | Wallach | |
| 5,631,012 A | 5/1997 | Shanni | |
| 5,643,899 A * | 7/1997 | Elias et al. | 514/171 |
| 5,665,379 A | 9/1997 | Herslof et al. | |
| 5,733,572 A * | 3/1998 | Unger et al. | 424/450 |
| 5,776,480 A | 7/1998 | Candau et al. | |
| 5,817,856 A | 10/1998 | Tirosh et al. | |
| 5,820,873 A | 10/1998 | Choi et al. | |
| 5,942,245 A | 8/1999 | Katinger et al. | |
| 5,993,830 A | 11/1999 | Freij | |
| 6,132,763 A | 10/2000 | Fisher | |
| 6,153,209 A | 11/2000 | Vega et al. | |

(Continued)

FOREIGN PATENT DOCUMENTS

CA 2281430 * 9/1999

(Continued)

OTHER PUBLICATIONS

Database CA Chemical Abstracts Service: XP002341829. Assn. #134:168089.

(Continued)

Primary Examiner — Blessing Fubara
(74) Attorney, Agent, or Firm — Moser Taboada

(57) ABSTRACT

The invention relates to a water-based delivery system for an active substance, characterized by enhancing skin barrier restoration in the stratum corneum comprising water, a fatty acid, cholesterol, a ceramide and at least one skin lipid precursor.

73 Claims, 7 Drawing Sheets

U.S. PATENT DOCUMENTS

| | | |
|---|---|---|
| 6,238,694 B1 | 5/2001 | Gasco |
| 6,419,949 B1 | 7/2002 | Gasco |
| 6,497,888 B1 | 12/2002 | Morancais et al. |
| 6,586,000 B2 | 7/2003 | Luo et al. |
| 6,730,288 B1 | 5/2004 | Abram |
| 6,824,785 B1 | 11/2004 | Kitson et al. |
| 6,932,963 B2 | 8/2005 | Perricone |
| 6,936,272 B2 | 8/2005 | Martin et al. |
| 2002/0048596 A1 | 4/2002 | Cevc |
| 2002/0064524 A1 | 5/2002 | Cevc |
| 2003/0099694 A1 | 5/2003 | Cevc et al. |
| 2004/0009213 A1 | 1/2004 | Skold |
| 2004/0071767 A1 | 4/2004 | Cevc et al. |
| 2005/0123897 A1 | 6/2005 | Cevc et al. |
| 2005/0129722 A1 | 6/2005 | Skold |
| 2007/0031483 A1 | 2/2007 | Cevc |
| 2007/0042030 A1 | 2/2007 | Cevc |
| 2007/0184114 A1 | 8/2007 | Cevc |
| 2009/0081139 A1 | 3/2009 | Skold |

FOREIGN PATENT DOCUMENTS

| | | |
|---|---|---|
| CA | 2281430 A | 9/1999 |
| EP | 0087993 A | 9/1983 |
| EP | 0711558 A1 | 5/1996 |
| EP | 0711588 A1 | 5/1996 |
| EP | 1092428 A | 4/2001 |
| FR | 2794366 A | 12/2000 |
| JP | 2001-048721 * | 2/2001 |
| JP | 200104874 A | 2/2001 |
| JP | 2001048721 | 2/2001 |
| NZ | 254392 | 7/1997 |
| NZ | 254392 A | 7/1997 |
| WO | 9637192 A | 11/1996 |
| WO | 9637192 A1 | 11/1996 |
| WO | 9817253 A | 4/1998 |
| WO | 9817253 A1 | 4/1998 |

OTHER PUBLICATIONS

Silvander, et al. "A Method to Detect Leakage of DNA Intercalators through Liposome Membranes" Analytical Biochemistry 242, 40-44 (1996) Article No. 0425, May 6, 1996.

Igarashi, et al. (Advanced Drug Delivery Reviews 20, p. 147-154, 1996).

* cited by examiner

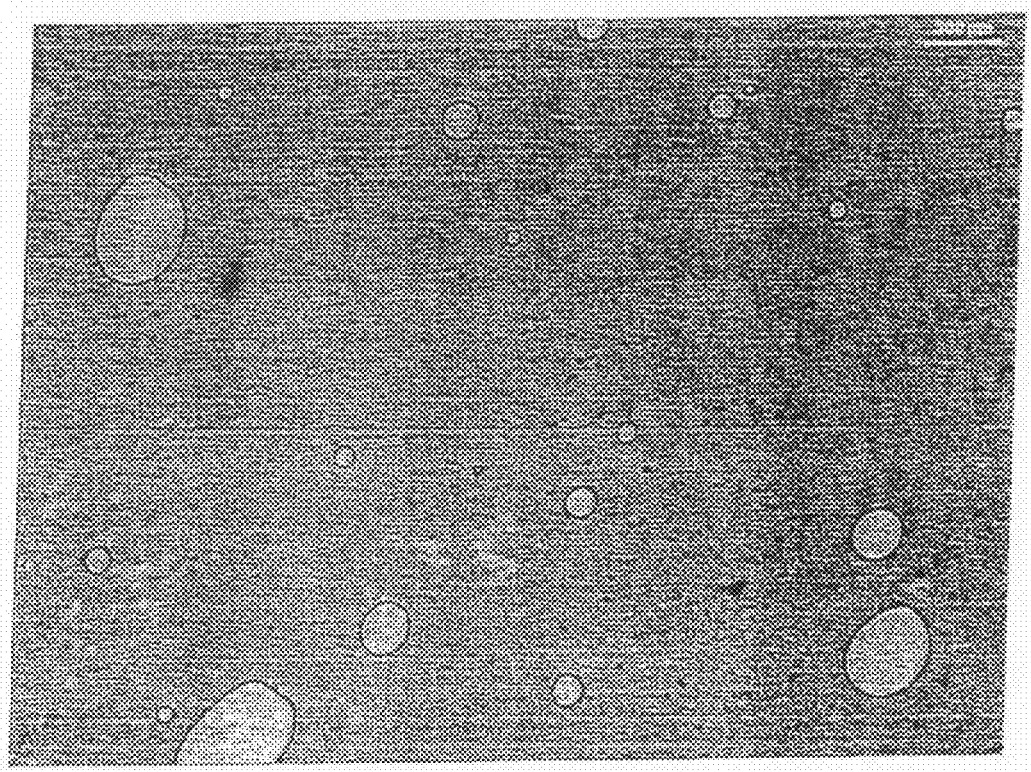
FIGURE 5 - A microscope image of the foam phase.

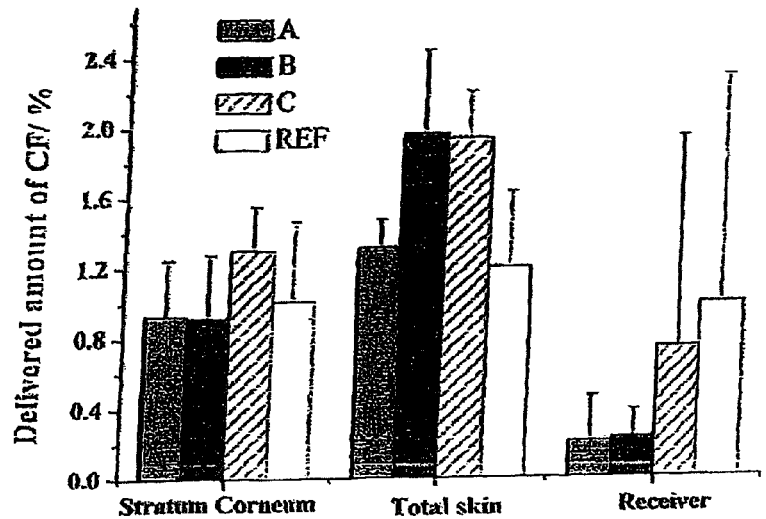
FIGURE 6 - Amount of CF detected in stratum corneum, total skin and the receiver compartment.
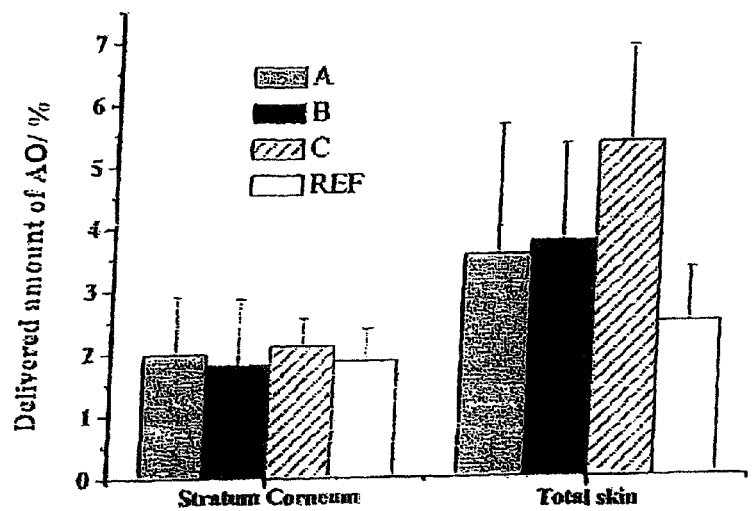
FIGURE 7 - Amount of AO detected in stratum corneum and total skin.

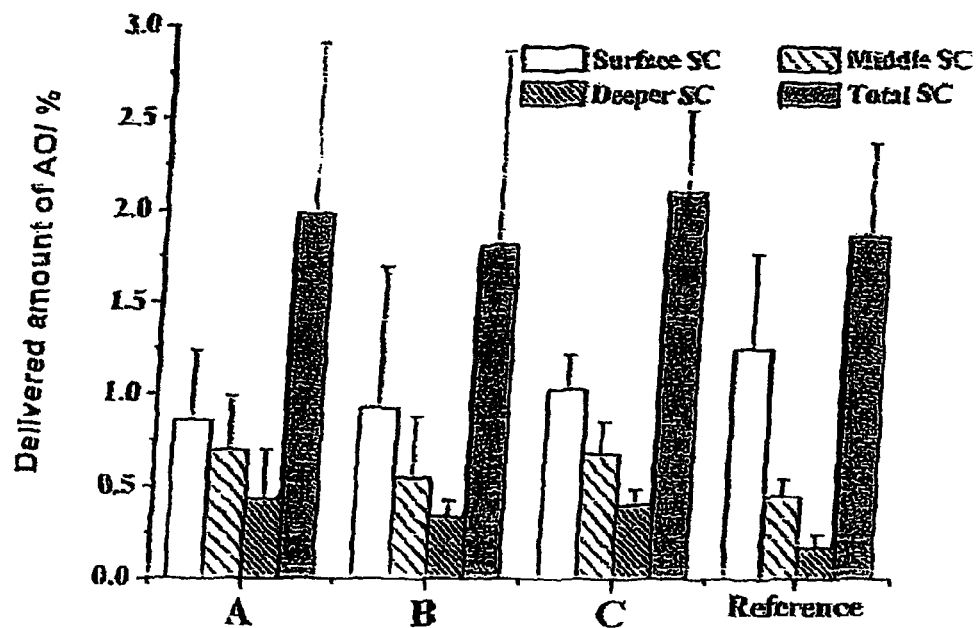
FIGURE 8 - Amount of AO detected at different depth of stratum corneum.
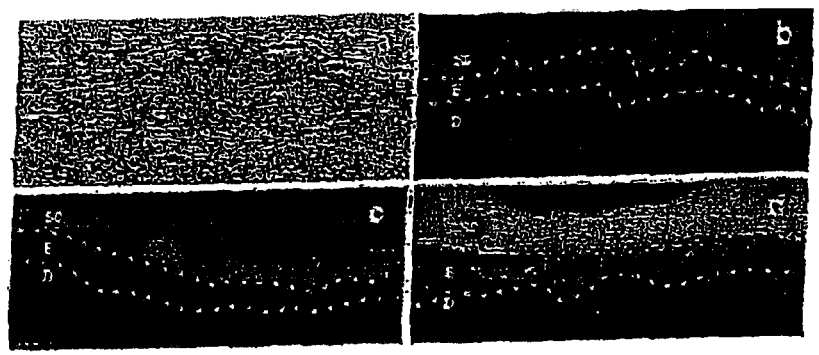
FIGURE 9 - Fluorescence microscopy images.

WATER-BASED DELIVERY SYSTEMS

CROSS-REFERENCE TO RELATED APPLICATIONS

This application claims the benefit of U.S. patent application Ser. No. 10/388,371, filed Mar. 13, 2003; and U.S. Provisional Application No. 60/365,059, filed Mar. 13, 2002, both of which are incorporated herein by reference.

FIELD OF THE INVENTION

The present invention relates to a novel topical and mucosal delivery systems for drugs or any other active substance.

BACKGROUND OF THE INVENTION

The main demands on human skin are to prevent loss of water, and to prevent water and other matter of the environment from entering the body indiscriminately. The human skin thus forms a selectively permissible physical barrier between the human body and its surroundings.

The barrier function has been shown to reside in the stratum corneum. The stratum corneum is the topmost layer of the skin, and is built of corneocytes. Corneocytes are cells that contain extensively cross-linked proteins, surrounded by a highly resistant cell envelope. The corneocytes are embedded in a bed of specific lipid structures of long chain lipids. These long chain lipids are organized as bilamellar structures stacked on top of each other. The bilamellar structures fill the intercellular spaces between the corneocytes.

To account for the skin's barrier properties, and for its selective hydrophilic and hydrophobic pathways, the skin has been described as a mosaic barrier model. This model envisages barrier lipids to exist predominantly in crystalline (gel) form. Such a form provides water impermeable domains, which are surrounded by so-called grain borders of lipids in a liquid crystalline state. This arrangement provides an effective, water tight barrier that still allows a minute but controlled loss of water through the liquid crystalline interdomains. This controlled water loss is enough to keep the keratin of the stratum corneum hydrated. The liquid character of the interdomain grain borders allows passage of hydrophilic and hydrophobic molecules on down-hill gradients, i.e. passage by passive diffusion.

Dermal delivery systems are compositions which deliver active substances to, or through, the skin. These compositions typically contain skin permeation enhancers. Permeation enhancers may induce structural transformations of the bilamellar structure in the liquid crystalline interdomain regions, and thus promote transdermal delivery of, for example, pharmacological substances.

Typical dermal delivery systems have an alcohol or petroleum base, with little consideration given to the biological properties of the vehicle itself. For example, emulsified fatty acids can inherit certain detergent properties if their structure is significantly altered from those in the normal skin. The detergent properties can lead to disruption of the normal barrier function, which is counteractive to the potential benefit of the delivery system. Disruption of the normal barrier function often causes the stratum corneum to lose its natural potential to function properly as a barrier. As a result, the skin becomes either too dry or too permeable to environmental substances.

Other conventional delivery systems that are thought to protect the skin from harmful substances are barrier ointments. The purpose of barrier ointments is to provide a film, and thereby create a layer which is impermeable to environmental substances. Due to the impermeability, though, these ointments both increase the body temperature of the treated body part, as well as prevent perspiration, and thus render an uncomfortable sensation.

The dermal delivery systems described above are not formulated to deliver a substance to, or through, the human skin without permanently disrupting the stratum corneum's natural barrier function.

SUMMARY OF THE INVENTION

In one embodiment, the invention relates to a water-based delivery system for an active substance, characterized by enhancing skin barrier restoration in the stratum corneum comprising water, a fatty acid, cholesterol, and a ceramide. In another embodiment, the delivery system also comprises at least one skin lipid precursor.

In an additional embodiment, the invention relates to delivery system for an active substance comprising water and lipophilic components, wherein the lipophilic components comprise fatty acids, cholesterol, and a ceramide/phospholipid portion, and wherein the lipophilic components are in the form of lipid particles, and gas spheres or vesicles. This delivery system can also comprise at least one skin lipid precursor.

BRIEF DESCRIPTION OF DRAWINGS

FIG. 5 is a microscopic image of the foam phase.

FIG. 6 is a graph showing the amount of 5(6)-carboxyfluorescein (CF) detected in the stratum corneum, total skin and the receiver compartment for four different formulations, CF-A, CF-B, CF-C and the reference.

FIG. 7 is a graph showing the amount of acridine orange 10-nonyl bromide (AO) detected in the stratum corneum, total skin and the receiver compartment for four different formulations, AO-A, AO-B, AO-C and the reference.

FIG. 8 is a graph showing the amount of AO detected at different depths of the stratum corneum.

FIG. 9 are fluorescent microscope images showing in vivo results for the penetration of active ingredients into the skin using the delivery systems: a) frozen section of normal skin stained with hematoxylin viewed by light microscopy, b) auto fluorescence of untreated epidermis, c) auto fluorescence of petrolatum with penetration only into stratum corneum, d) auto fluorescence of the total lipid formulation (variation A) with penetration into the viable epidermis and dermis.

DETAILED DESCRIPTION OF INVENTION

Figure 1:
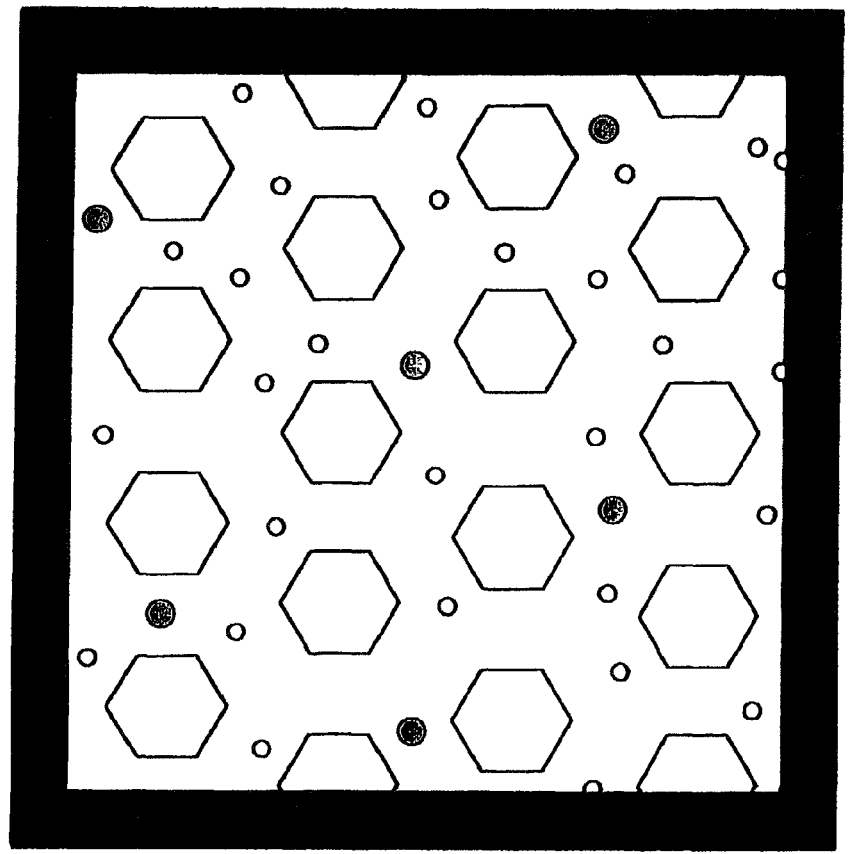
FIG. 1 is a diagram showing the gas spheres, lipid particles, vesicles and hydrophilic phase of the delivery systems.

The present invention provides an improved topical delivery system (skin preparation) formulated to deliver a substance to, or through, the human skin without permanently disrupting the stratum corneum's natural barrier function. Additionally, the topical delivery system of the present invention provides unique skin barrier restoration properties.

All percentages given below are indicated in percent by weight. All numbers are approximate.

The topical delivery system of the present invention is a water-based formulation comprising hydrophilic and lipophilic components. In a preferred embodiment, the delivery system comprises a water content exceeding 50%, such as more than 55%, 60%, 65%, 70%, 75%, 76%, 77%, 78%, 79%, 80%, 85%, 87%, 90%, 94%, 95% and 98%. Preferably, the water content is between 60-80%, more preferably, between 70 and 80%.

The topical delivery system is preferably designed, in its choice and composition of lipids, to resemble the normal lipid organization of the stratum corneum (horny layer), as much as possible. Upon administration, the system (formulation) blends with the lipids naturally present in the stratum corneum, and easily penetrates the lipid bilayer of the skin. In doing so, the system carries along with it one or more active substances to be administered. The system enhances penetration of active substances into and/or through the stratum corneum, while the normal barrier properties of the stratum corneum are left intact, and/or are even functionally enhanced.

The lipophilic component (i.e. lipids) of the system comprises fatty acids, cholesterol and a ceramide/phospholipid portion. The lipids are similar to those which make up the normal stratum corneum. The preferred ratio of the ceramide/phospholipid portion:cholesterol:fatty acid is in the range of approximately 2:1:1.5 to approximately 2.95:0.5:0.5. Preferably, for example, the ratio is approximately 2:1:1; more preferably the ratio is approximately 2.35:1:1.

The fatty acids of the present invention can be any fatty acid, mixtures of fatty acids, salts of fatty acids, or mixtures of fatty acids and salts of fatty acids. The fatty acids can be saturated or unsaturated. Additionally, the fatty acids can comprise precursors of fatty acids. In a preferred embodiment, the fatty acids comprise ten, twelve, fourteen, sixteen, eighteen, twenty, twenty-two, or twenty-four carbon atoms, or any mixture of such fatty acids. A fatty acid mixture with a predominant portion of fatty acids which comprise a chain of sixteen or eighteen carbon atoms is most preferred.

For example, the delivery system can be prepared from a mixture of fatty acids of the following composition: at most about 2% of a component comprising a chain of fourteen carbon atoms, between about 47 and about 52% of a component comprising a chain of sixteen carbon atoms, between about 43 and about 48% of a component comprising a chain of eighteen carbon atoms, and at most about 1% of a component comprising a chain of twenty carbon atoms.

Examples of suitable saturated fatty acids for use in the delivery system include lauric acid, myristic acid, palmitic acid, stearic acid, arachidic acid, behenic acid, and lignoceric acid. Examples of suitable unsaturated fatty acids include oleic acid, palmitoleic acid, linoleic acid, linolenic acid, and arachidonic acid. Preferably, the delivery system contains an essential portion, such as about 90%, of such fatty acids.

The preferred fatty acids are the essential fatty acids (EFAs). EFAs are essential for the plasma membrane formation of all cells. In keratinocytes, EFA deficiency makes cells hyperproliferative. Supplementation of EFAs reverses the hyperproliferation. EFAs also enhance lipid biosynthesis of the epidermis and provide lipids for the barrier formation of the epidermis. The essential fatty acids are preferably chosen from linoleic acid, γ-linolenic acid, homo-γ-linolenic acid, columbinic acid, eicosa-n-6,9,13)-trienoic acid, arachidonic acid, timnodonic acid, hexaenoic acid, and mixtures thereof.

The delivery system also comprises cholesterol, or derivatives of cholesterol such as, for example, lipid esters of cholesterol.

The ceramide/phospholipid portion can comprise 100% ceramide, 100% phospholipids, or any other percent combination of ceramide and phospholipids. For example, the ceramide/phospholipid portion can comprise 95% ceramide and 5% phospholipids, 90% ceramide and 10% phospholipids, 85% ceramide and 15% phospholipids, or 80% ceramide and 20% phospholipids.

Since the system preferably resembles the lipid composition of the skin as much as possible, it is desirable to use 100% ceramide in the ceramide/phospholipid portion. However, from an economic point of view, the addition of phospholipid to the ceramide/phospholipid portion may be a more suitable choice.

The ceramide component of the delivery system can be any ceramide or any mixture of ceramides. In this specification, ceramides include pseudoceramides and neoceramides.

For example, the ceramide may be any of ceramide 1-7; and/or mixtures thereof. Some specific examples of ceramides include ceramide 1, ceramide 3, ceramide 4, ceramide 5, ceramide 6A, cerebrosides and ceramide 6B. Preferably, the ceramides used in the systems are ceramides 1, 3 and 6. An example of a formulation that comprises these ceramides is SK-Influx® (Cosmoferm).

Some examples of pseudoceramides include:
N-(2-hydroxyoctadecyl)-N-(2-hydroxyethyl)hexadecanamide
N-(2-hydroxyoctadecyl)-N-(2-hydroxyethyl)propanamide
N-(2-hydroxyhexadecyl)-N-(2-hydroxyethyl)butanamide
N-(2-hydroxyhexadecyl)-N-(2-hydroxyethyl)heptanamide
N-(2-hydroxyoctadecyl)-N-(2-hydroxyethyl)ethanamide
N-(2-hydroxyoctadecyl)-N-2-O-glucopyranosyl)ethylpentanamide
N-(2-hydroxydodecyl)-N-(2-hydroxyethyl)hexanamide
N-(2-hydroxydodecyl)-N-(2-hydroxyethyl)-2butylhexanamide
N-(2-hydroxyhexadecyl)-N-(2-hydroxyethyl)ethanamide
N-(2-hydroxydodecyl)-N-(2-hydroxyethyl)-2-hydroxyhexanamide
N-(2-hydroxytetraadecyl)-N-(2-hydroxyethyl)propanamide
N-(2-hydroxyhexadecyl)-N-(2-sulfoethyl)hexadecanamide
N-(2-hydroxyoctadecyl)-N-(2-phosphoethyl)butanamide
N-(2-hydroxyoctadecyl)-N-(2-hydroxyethyl)-2-hydroxypropanamide
N-(2-hydroxy-3-octadecyloxypropyl)-N-(2-hydroxyethyl)hexadecanamide
N-(2-hydroxy-3-nonanyloxypropyl)-N-(2-hydroxyethyl)propanamide
N-(2-hydroxyoctadecyl)-N-(2-hydroxyethyl)-2-hydroxypropanamide
N-(2-hydroxy-3-hexadecyloxypropyl)-N-(2-hydroxyethyl)hexadecanamide
N-(2-hydroxy-3-octadecyloxypropyl)-N-(2-hydroxyethyl)butanamide
N-(2-hydroxy-3-hexadecyloxypropyl)-N-(2-hydroxyethyl)ethanamide
N-(2-hydroxy-3-dodecyloxypropyl)-N-(2-sulfohydroxyethyl)decanamide
N-(2-hydroxy-3-decyloxypropyl)-N-(2-hydroxyethyl)hexanamide
N-(2-hydroxy-3-octadecyloxypropyl)-N-(2-hydroxyethyl)hexadecanamide
N-(2-hydroxy-3-dodecyloxypropyl)-N-(2-hydroxyethyl)butanamide N-(2-hydroxy-3-octadecyloxypropyl)-N-(2-hydroxyethyl) co-o-linoleoyldocosanamide
N-(2-hydroxy-3-dodecyloxypropyl)-N-(2-hydroxyethyl) propanamide
N-(2-hydroxy-3-hexadecyloxypropyl)-N-(2-hydroxyethyl)-2-methylpropanamide
N-(2-hydroxy-3-tetraadecyloxypropyl)-N-(2-hydroxyethyl) ethanamide
N-(2-hydroxy-3-dodecyloxypropyl)-N-(2-hydroxyethyl) heptanamide
N-(2-hydroxy-3-hexadecyloxypropyl)-N-(2-phosphoethyl) hexadecanamide
N-(2-hydroxy-3-dodecyloxypropyl)-N-(2-hydroxyethyl) propanamide
N-(2-hydroxy-3-octadecyloxypropyl)-N-(2-)-glucopyranosyl)ethyl-2-hydroxy pro-panamide
N-(2-hydroxy-3-octyloxypropyl)-N-(2-hydroxyethyl)pentanamide Some examples of neoceramides include:
N-(2,3-dihydroxypropyl)-N-(hexadecyl)butanamide
N-(2,3-dihydroxypropyl)-N-(tetradecyl)ethanamide
N-(2,3-dihydroxypropyl)-N-(hexadecyl)-2-hydroxypropanamide
N-(2,3-dihydroxypropyl)-N-(octadecyl)butamide
N-(2,3-dihydroxypropyl)-N-(2-ethylhexadecyl)hexanamide
N-(2,3-dihydroxypropyl)-N-(hexadecyl)-2-hydroxyoctanamide
N-(2,3-dihydroxypropyl)-N-(3-methylhexadecyl)ethanamide
N-(2,3-dihydroxypropyl)-N-(dodecyl)butanamide
N-(2,3-dihydroxypropyl)-N-(hexadecyl)-2-hydroxyhexanamide
N-(2-hydroxy-3-O-glucopyranosylpropyl)-N-(hexadecyl) octanamide
N-(2-hydroxy-3-phosphopropyl)-N-(octadecyl)ethanamide
N-(2-hydroxy-3-sulfopropyl)-N-(hexadecyl)butanamide
N-(2-hydroxy-3-O-glucopyranosylpropyl)-N-(hexadecyl) decanamide
N-(2,3-dihydroxypropyl)-N-(heptadecyl)ethanamide
N-(2,3-dihydroxypropyl)-N-(3-methylhexadecyl)ethanamide
N-(2,3-dihydroxypropyl)-N-(heptadecyl)butanamide
N-(2,3-dihydroxypropyl)-N-(6-dodecenyl)hexadecanamide
N-(2,3-dihydroxypropyl)-N-(2-methylhexadecyl)-2-hydroxy-ethanamide
N-(2,3-dihydroxypropyl)-N-(cctadecyl)-2-hydroxypropanamide
N-(2-hydroxy-3-O-glucopyranosylpropyl)-N-(heptadecyl)-ethanamide
N-(2-hydroxy-3-sulfopropyl)-N-(dodecyl)heptanamide
N-(2,3-dihydroxypropyl)-N-(tetradecyl)-4-hydroxybutanamide
N-(2,3-dihydroxypropyl)-N-octadecyl)-(t)-O-linoleoyl-docosanamide
N-(2,3-dihydroxypropyl)-N-(linoleyl)ethanamide
N-(2,3-dihydroxypropyl)-N-(oleyl)-2-hydroxy-heptanamide
N-(2,3-dihydroxypropyl)-N-iyiodecyl)-(t)-O-linoleoyl-docosanamide
N-(2,3-dihydroxypropyl)-N-(octadecyl)-3-hydroxybutanamide
N-(2-phospho-3hydroxypropyl)-N-(heptadecyl)butanamide
N-(2,3-dihydroxypropyl)-N-(2-methylheptadecyl)propanamide
N-(2,3-dihydroxypropyl)-N-(3-ethylheptadecyl)butanamide
N-(2-sulfo-3-hydroxypropyl)-N-(1-octadecyl)ethanamide
N-(2,3-dihydroxypropyl)-N-octadecyl)propanamide
N-(2,3-dihydroxypropyl)-N-(dodecyl)decanamide
N-(2,3-dihydroxypropyl)-N-(3-ethyldodecyl)butanamide
N-(2-O-glucopyranosyl-3-hydroxy propyl)-N-(heptadecyl) butanamide
N-(2,3-dihydroxypropyl)-N-(oleyl)-2-hydroxypropanamide
N-(2,3-dihydroxypropyl)-N-(linoleyl)-2-hydroxyheptanamide
N-(2,3-dihydroxypropyl)-N-(dodecyl)-2-hydroxyoctanamide
N-(2,3-dihydroxypropyl)-N(hexadecyl)-2-methylheptanamide
N-(2,3-dihydroxypropyl)-N-(octadecyl)-2-hydroxypentanamide
N-(2,3-dihydroxypropyl)-N-(2-methylhexadecyl)-2-hydroxyheptanamide
N-(2,3-dihydroxypropyl)-N-(linoleyl)-2-hydroxypropanamide
N-(2;3-dihydroxypropyl)-N-(tetradecyl)ethanamide.

The phospholipid component may contain any phospholipid or mixtures of phospholipids. Preferably the phospholipid component comprises phosphatidylcholine (PC). Other examples of phospholipids include distearoylphosphatidylcholine (DSPC 18), phosphatidic acid, inositol phosphate, phosphatidylglycerol, phosphatidylinositol, phosphatidylserine, and phosphatidylethanolamine.

Additionally, the phospholipid component can comprise one or more lysophospholipids. Lysophospholipids are single chain phospholipids. Examples of lysophospholipids include lysophosphatidylcholines, such as monopalmitoylphosphatidylcholine (MPPC); lysophosphatidylglycerols; lysophosphatidylethanolamines; lysophosphatidylinositols; lysophosphatidylserines; and lysophosphatidic acid. Mixtures of different types of phospholipids and/or lysophospholipids can also be used.

Examples of phospholipid components include formulations which are sold by Degussa BioActives under the following names: Epikuron 200SH, Epikuron 200 and Epikuron 170. All these formulations comprise phospholipids, e.g., soya phosphatidylcholines (PC), and fatty acids. These formulations differ in the saturation and chain length of their constituent phospholipids and fatty acids.

EPIKURON® 200 SH comprises about 95% PC and 1.2% lysophosphatidylcholine. The phospholipids used in this formulation are saturated, long-chain phospholipids. Saturated phospholipids prevent leakage of active substances through the vesicular bilayer to a greater extent than unsaturated phospholipids do. Also, saturated phospholipids are more stable, both mechanically and chemically. The fatty acids in EPIKURON® 200 SH are all saturated fatty acids, and are mainly stearic fatty acid.

EPIKURON® 200 comprises about 95% PC and 3% lysophosphatidylcholine. The phospholipids used in this formulation are mainly unsaturated. Also, about 85% of the fatty acids are unsaturated. The fatty acids are mainly linoleic acid. This formulation provides enhanced penetration.

EPIKURON® 170 comprises PC and other phospholipids such as phosphatidylethanolamine (PE). The phase behaviour of PE is different from PC because of the smaller head group area in PE. In particular, PE forms reversed hexagonal phases instead of lamellar phases in excess water and at high temperatures. Also, about 85% of the fatty acids in EPIKURON® 170 are unsaturated. The fatty acids are mainly linoleic acid.

The chain melting temperature for phospholipids is the temperature at which the transition from solid phase to liquid crystalline phase of the lipid bilayers occurs. The chain melting temperature decreases with increasing unsaturation and decreasing chain length of the phospholipid. In the case of saturated long-chained phospholipids, the addition of cholesterol lowers this temperature. In the case of highly unsaturated phospholipids, the addition of cholesterol has the opposite effect than for saturated phospholipids.

If there is a need to change the properties of the formulation, the choice of phospholipid is an important component to consider, since different phospholipids give rise to varying characteristics of the formulation.

In a preferred embodiment, the present system also comprises skin lipid precursors. The lipid precursors include any compound that promotes in situ cholesterol, ceramide or sphingolipid synthesis. The preferred lipid precursors are mevalonic acid, which promotes in situ cholesterol synthesis; and 25-hydroxycholecalciferol, which promotes in situ ceramide synthesis in the skin. Other preferred precursors are palmitoyl CoA and serine, which together are converted to 3-ketosphinganine, which promotes in situ ceramide synthesis in the skin.

By the promotion of in situ cholesterol and ceramide synthesis in the skin, the overall content of lipid in the system can be maintained in a range as low as approximately 2-20%. Therefore, the water content of the delivery system can be as high as 80-98%. The high water content enables the skin to "breathe" normally, and enhances its ability to restore its normal barrier function rapidly.

Other lipid precursors useful in the present invention include, for example: acylceramides; deoxyacetein cimifugoside, adapalene, adenosine, aloe derived lectins, 3-aminopropyl dihydrogen phosphate, anise extracts, ascorbic acid and derivatives thereof, ascorbyl palmitate, asiatic acid, benzoic acid derivatives, biotin, butanoyl betulinic acid, cathecholamines, coenzyme Q10, dehydrocholesterol, dehydroascorbic acid and derivatives thereof, estrogen and derivatives, eythrobic acid, genistein, lipoic acid, 4-methoxysalicylic acid, N-acetylcysteine, panthetine, pregnenolone and derivatives, retinal, retinoates, retinal, retinyl acetate, retinyl glucuronate, retinyl linoleate, retinyl palmitate, retinyl proprionate, phytosphingosine, sphingosine, and others.

Preferably, an alkaline compound, or buffer system, is included in the formulation to adjust the pH. Examples of alkaline compounds include triethanolamine (TEA), sodium hydroxide, sodium acetate, and sodium bicarbonate. Examples of buffer systems include carbonic acid/potassium carbonate, phosphoric acid/potassium phosphate, and acetic acid/sodium acetate.

The fatty acids of the final delivery system can be in a free state or can form a salt. The portion of fatty acids which is in a free state is partially dependent on the pH of the formulation. In general, the level of free fatty acid increases as the pH of the formulation decreases. Depending upon the particular use of the formulation, the pH of the formulation can vary. Preferably, the pH of the formulation is about 6.5 to 7.8.

In a preferred embodiment, the delivery system comprises triethanolamine (TEA). It is preferred to adapt the molar ratio between the fatty acids and triethanolamine to enable a certain portion of the fatty acids in the final delivery system to form a triethanolaminium salt, while another portion of the acid exists as free fatty acid. Preferably, the delivery system is prepared from fatty acids and triethanolamine in which the molar ratio of the fatty acids to the triethanolamine is higher than about 2:1, preferably higher than about 3:1.

In a preferred embodiment, the delivery system comprises a combined content of a fatty acid, cholesterol, a ceramide/ phospholipid portion, and skin lipid precursors between about 2-20%. A preferred low end of this range is about 2%, 3%, 4%, 5%, 6%, 7% or 8%. A preferred high end of this range is about 13%, 14%, 15%, 16%, 17%, 18%, 19% and 20%.

In another preferred embodiment, the amounts of the components of the delivery system are as follows: fatty acid: 0.5-10%; cholesterol: 0.5-10%; a ceramide/phospholipid portion: 0.005-20%; and lipid precursors: 0.000001-10%.

In a preferred embodiment, the formulation does not contain any irritating ingredients. Examples of irritating ingredients include alcohols, such as isopropanol and ethanol; short chain fatty acids; and detergents. Preferably, the formulation contains less than 10% alcohol, more preferably less than 5% alcohol, most preferably less than 1% alcohol, and optimally no alcohol.

Without the intention to limit the scope of the invention, a possible theory explaining the mechanical properties of the delivery system follows. The administered formulation easily penetrates the lipid bilayer of the skin. In doing so, the system creates a temporary and reversible state of enhanced atrophy among the lipid components of the bilayer. The enhanced atrophy in itself then gives rise to either a) enhanced energy levels, wherein the energy could promote active transport of the to-be-carried substances into the skin, and/or b) creates naturally and reversibly occurring holes and disorganized patches in the lipid bilayer through which the active substances could then pass more easily. It is very well feasible that the temporary disarray in the lipid bilayer will temporarily break up the organized structure of the bilayer and create micelles of lipids with areas between them, or surrounding them, through which lipophobic/hydrophilic substances and/or compositions can enter through the stratum corneum. As the lipid composition of the formulation resembles the natural lipid composition of the skin, the so introduced new lipids will after a short time of creative chaos easily blend in with the natural lipid building stones of the lipid bilayer, and thus not permanently damage the barrier function of the skin.

Following the temporary disarray in the lipid bilayer, the normal barrier function of the cornea stratum rapidly returns. (That is, the skin barrier restoration is rapid.) The rapid return may be enhanced by the lipid precursors of the formulation. For example, the in situ promotion of cholesterol synthesis in the stratum corneum, the in situ promotion of ceramide synthesis in the stratum corneum, and/or the in situ promotion of sphingolipid synthesis in the stratum corneum may allow for the rapid skin barrier restoration.

A delivery system according to the present invention preferably comprises a combination of:

| | |
|---|---|
| Fatty Acid (C16-24) | 0.5-10% |
| Phospholipid | 0.5-10% |
| Cholesterol | 0.5-7% |
| Lipid precursor: Mevalonic acid and/or 25-Hydroxycholecalciferol | 0.000001-10% |
| Ceramide | 0.005%-7% |

(Not all components are present are 0%.)

Another preferred embodiment of the delivery system comprises:

| | |
|---|---|
| Fatty Acid (C16-24) | 0.5-10% |
| Phospholipid | 0.5-10% |
| Cholesterol | 0.5-7% |

-continued

| | |
|---|---|
| Lipid precursor: | 0.000001-10% |
| Mevalonic acid and/or | |
| 25-Hydroxycholecalciferol | |
| Ceramide | 0.005%-7% |
| Glycerine | 0-5% |
| Propylene glycol | 0-48% |
| PVP (e.g., M weight 40.000) | 0-5% |
| TEA | 0-3% |

(Not all components are present are 0%.)

An even more preferred embodiment of the delivery system comprises:

| | |
|---|---|
| Fatty Acid (C16-24) | 2% |
| Phospholipid | 4.5% |
| Cholesterol | 2% |
| Lipid precursor: | 0.000001-10% |
| Mevalonic acid and/or | 1% or 0.01% |
| 25-Hydroxycholecalciferol | 0.015% or 0.0015% |
| Ceramide 3 | 0.015% |
| Glycerine | 3% |
| Propylene glycol | 4% |
| PVP (M weight 40.000) | 2% |
| TEA | 0.5% |

An even more preferred embodiment of the delivery system comprises:

| | |
|---|---|
| Fatty Acid (C16-24) | 2% |
| Phospholipid | 4.5% |
| Cholesterol | 2% |
| Lipid precursor: | 0.000001-10% |
| Mevalonic acid and/or | 1% or 0.01% |
| 25-Hydroxycholecalciferol | 0.015% or 0.0015% |
| Ceramide 3 | 0.015% |
| Glycerine | 3% |
| Propylene glycol | 4% |
| PVP (M weight 40.000) | 2% |
| TEA | 0.5% |
| Ceramide 1 | 0.025% |

For delivery systems formulated for dry skin conditions, such as, for example, eczema, psoriasis and shingles, the amount of the lipid precursors are preferably increased by a factor of about three to about six, more preferably by a factor of about four to five, vis-à-vis systems not formulated for dry skin conditions. For example, a system for a dry skin condition can comprise about four to five times as much mevalonic acid and/or 25-hydroxycholecalciferol as a system not made for a dry skin condition. For example, a dry skin system can comprise about 0.01% mevalonic acid and about 0.0015% 25-hydroxycholecalciferol vis-à-vis about 0.002% mevalonic acid and about 0.0003% 25-hydroxycholecalciferol in other type of systems.

The topical delivery system according to the present invention further comprises one or more cosmetically and/or therapeutically active substances. Active substances are defined as agents other than emollients and other than ingredients that merely improve the physical characteristics of the formulation.

Some general examples of active substances include sunscreens, tanning agents, skin anti-wrinkling agents, anti-dandruff agents, anti-acne agents, hair growth stimulants and vitamins. Therapeutically active substances include, but are not limited to, substances which treat conditions such as eczema, dry skin, itchy skin, fungal infection, acne, skin cancer, hair loss, louse infection, psoriasis, and skin lesions (i.e. wounds). Therapeutically active substances also include substances for transdermal delivery, for example, interleukin, hormones, vaccines, nicotine, interferon, pain killers, peptides, proteins and vitamins.

Active substances also include steroid hormones. Steroid hormones inhibit inflammation and hyperproliferation of the epidermis thus resulting in normalization of hypersensitive skin conditions. Examples of steroid hormones include, but are not limited to, glucocorticoids, androgens and estrogens.

Examples of sunscreens include those materials commonly employed to block ultraviolet light. Illustrative compounds are derivatives of PABA, cinnamate and salicylate. For example, octyl methoxycinnamate and 2-hydroxy-4-methoxybenzophenone (also known as oxybenzone) can be used. Octyl methoxycinnamate and 2-hydroxy-4-methoxybenzophenone are commercially available under the trademarks, Parsol MCX and Benzophenone-3, respectively. The exact amount of sunscreen employed in the systems can vary depending upon the degree of protection desired from the sun's UV radiation.

Examples of vitamins include vitamin A and vitamin E, preferably in the form of an ester of a fatty acid, such as vitamin A palmitate (retinyl palmitate) and vitamin E linoleate (tocopheryl linoleate). Other esters of vitamins A and E may also be utilized, such as any of the fatty acids mentioned above and below.

Preservatives may also be included in the formulations of the present invention. Suitable preservatives include alkyl esters of p-hydroxybenzoic acid, hydantoin derivatives, propionate salts, and a variety of quaternary ammonium compounds. Particularly preferred preservatives of this invention are methyl paraben, propyl paraben, imidazolidinyl urea, sodium dehydroxyacetate and benzyl alcohol. Preservatives are typically used in amounts up to about 2% by weight of the formulation. An example of a preservative is Phenonip®.

Other adjunct minor components may also be incorporated into the formulations of the present invention. These components may include thickeners, coloring agents, opacifiers and perfumes. For example, any thickening agent can be included in the formulation to adjust the viscosity of the formulation. Examples of suitable thickening agents include glycerol and xanthan gum. Some additional adjunct minor components include chalk, talc, Fullers earth, kaolin, starch, smectites clays, chemically modified magnesium aluminium silicate, organically modified montmorillonite clay, hydrated aluminium silicate, fumed silica, aluminium starch octenyl succinate and mixtures thereof. Amounts of these adjunct minor components may range anywhere from 0.001 up to 20% by weight of the formulation (i.e. composition). Additionally, to adjust the pH, bases can be included in the systems, e.g., sodium hydroxide and triethanolamine.

The delivery system can be in any form, such as a cream, a lotion, a gel, and an aerosol foam. The amount of certain adjunct minor components used in a particular formulation varies depending on the desired form of the delivery system, as would be known by a skilled artisan. For example, the amount of thickening agent used to prepare an aerosol foam formulation is about 10 to 20% of the amount used to prepare a cream formulation. Additionally, emulsifiers are added to an aerosol foam formulation, such as, for example, laureth 4.

In another embodiment, the present invention provides a mucosal delivery system formulated to deliver a substance to, or through, a human mucous membrane without permanently disturbing the integrity of the mucous membrane. The mucous membrane is the moist tissue that lines some organs and body cavities (such as nose, mouth, lungs, rectum, stomach and vagina) and secretes mucous. The mucosal delivery system comprises the lipophilic and hydrophilic components, as described above. The particular formulations of the mucosal delivery systems are varied to accommodate the particular environment of the mucosa, as would be known by a skilled artisan.

In a preferred embodiment, the lipophilic components of the topical or mucosal delivery system form three types of particles: gas spheres, vesicles, and lipid particles. These three types of particles are within a hydrophilic phase (i.e. aqueous medium). See FIG. 1.

Figure 2:
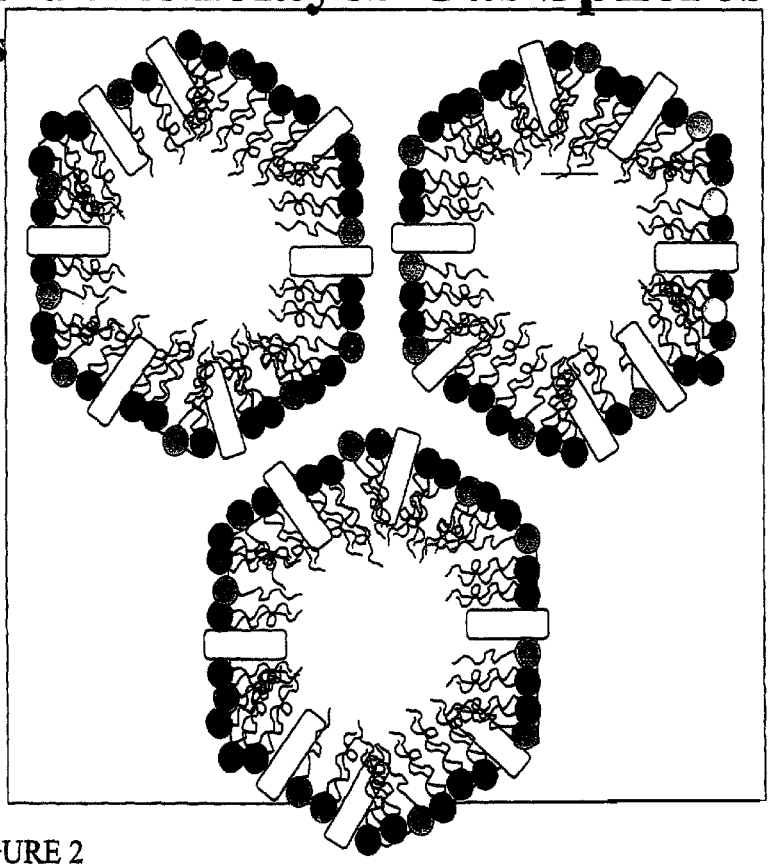
FIG. 2 is a diagram showing the components of the gas spheres of the delivery systems.

The gas spheres are lipid monolayers that enclose air bubbles. These monolayers are formed from the lipophilic components. Negatively charged carboxylate groups stud the outer surfaces of these gas spheres. See FIG. 2. Preferably, these gas spheres are approximately 1 μm to approximately 500 μm in diameter.

Figure 3:
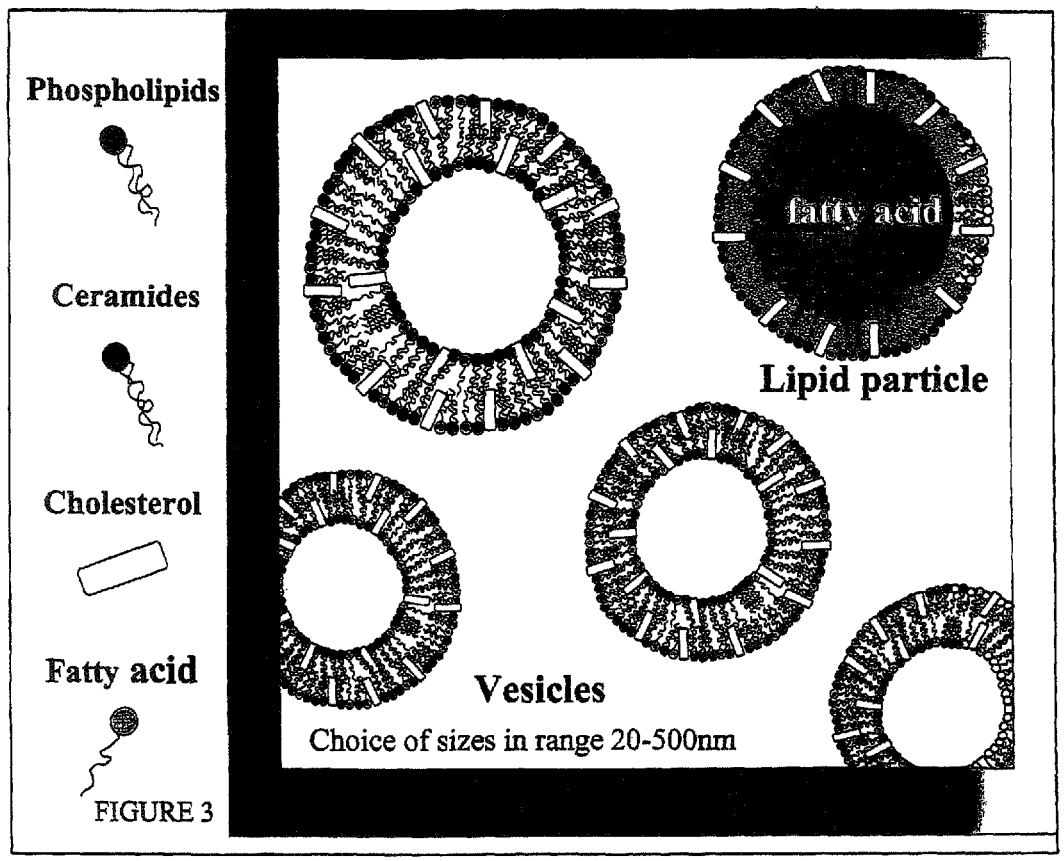
FIG. 3 is a diagram showing the components of the lipid particles and of the vesicles of the delivery systems.

The vesicles are lipid bilayers enclosing a hydrophilic core. These bilayers are formed from the lipophilic components. Negatively charged carboxylate groups stud the inner and outer surfaces of the vesicles. See FIG. 3. The vesicles can range from approximately 0.02 μm to approximately 0.5 μm in diameter, or from approximately 0.5 μm to approximately 2 μm in diameter, or from approximately 1 μm to approximately 2.5 μm in diameter. The diameter of a vesicle increases as the amount of an active ingredient incorporated into the vesicle increases.

The lipid particles are lipid monolayers enclosing fatty acids. These monolayers are formed from the lipophilic components. See FIG. 3. The lipid particles are less than approximately 1 to approximately 150 μm in diameter. The lipid particles may be in the form of individual lipid particles, or the lipid particles may aggregate to form crystals.

Figure 4:
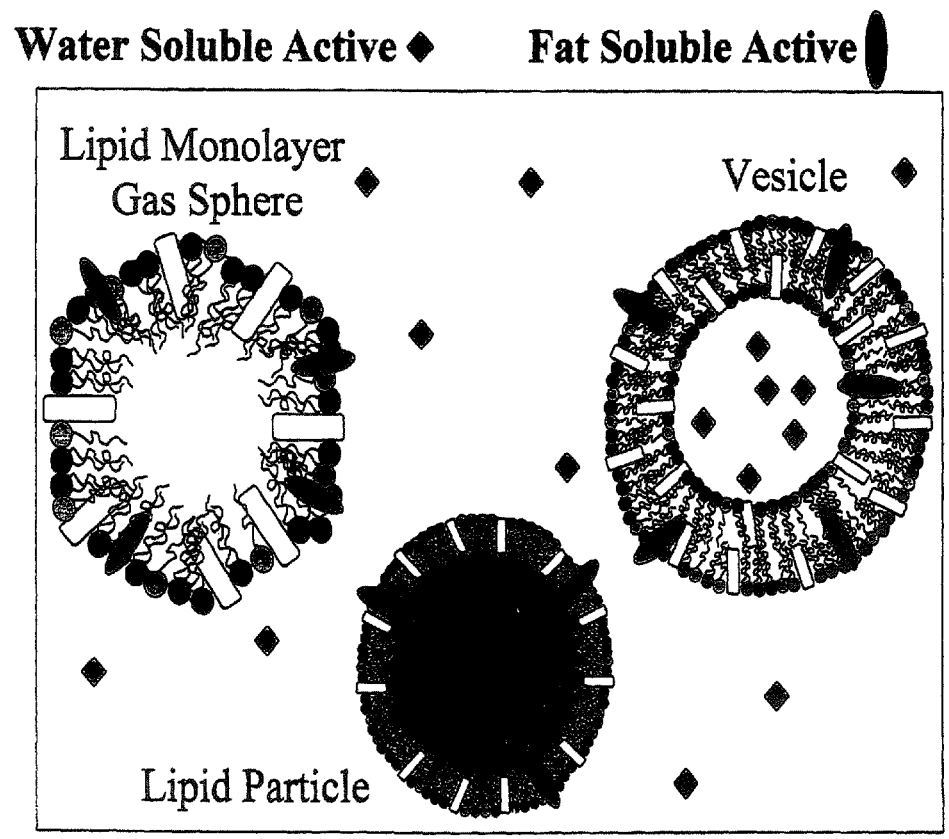
FIG. 4 is a diagram showing the location of active substances within the various microcompartments of the delivery systems.

The various particles of the delivery system provide microcompartments with different properties. Due to these different microcompartments, the delivery system can be used to deliver both hydrophilic and lipophilic active substances. For example, a water soluble active substance can be located in the hydrophilic core of the vesicles, or can be located in the hydrophilic phase of the system. A lipid soluble active substance can be located within the monolayer of the gas spheres, within the bilayer of the vesicles, or within the monolayer or within the core of the lipid particles. See FIG. 4.

Preferably, the delivery systems comprise three phases, i.e. a foam phase, a vesicle phase and a hydrophilic phase. The foam phase comprises the gas spheres and the lipid particles. The vesicle phase comprises the vesicles and the lipid particles. The hydrophilic phase comprises water and hydrophilic components.

In a preferred embodiment, the delivery system is produced from three portions (i.e. fractions), in particular a hydrophilic portion and two lipophilic portions. The two lipophilic portions comprise the lipophilic components as defined above. Both lipophilic portions are immersed in aqueous media. One portion is made into the foam phase. The other portion is made into the vesicle phase. The foam phase portion and the vesicle phase portion can be in a ratio from about 1:7 to about 7:1. Preferably, the foam phase portion and the vesicle phase portion are approximately equal in amount.

Preferably, the foam phase is formed by mixing the foam phase portion at about 65 to 85° C. The pH is set to the range of about 5.5 to 8.2. The mixing is performed under conditions so as to allow gas spheres to form. Mixing can be performed by using an mixing apparatus, such as, for example, an Ultra Turrax® (Ultra Turrax T 25, Janke & Kunkel IKA-Labortech-nik). The time and speed of mixing can vary. For example, Ultra-turraxing can be performed for one minute at a speed of 9500 rpm.

Preferably, the vesicle phase is formed by gently mixing the vesicle phase portion at about 65 to 85° C. More preferably, the vesicle phase is formed by homogenizing or sonicating the vesicle phase portion at about 65 to 85° C. The pH is set to the range of about 5.5 to 8.2. Preferably, the vesicle phase is produced under conditions which do not allow any gas to enter the formulation, such as in a vacuum.

Homogenization can be accomplished with, for example, a high pressure homogenizer or a sonicator. An example of a homogenizer is a Rannie homogenizer from APV. The pressure of the homogenizer can be set, for example, from about 10,000 to 40,000 psi. An example of a sonicator is Soniprep 150, manufactured by Sanyo Gallencamp Plc. Ultrasound radiation is transmitted by high frequency vibrations via a titanium alloy probe from a transducer that converts electrical energy to mechanical energy. The diameter of the probe tip can vary. An example of a diameter of a probe tip is about 9.5 mm. The amplitude at which the sonication can be performed can vary. An example of an amplitude is 10 microns for 30 minutes.

The lipid particles, and/or lipid particle crystals, form as a by-product of the formation of the foam phase and vesicle phase. In either the foam phase or vesicle phase, up to 30% of the lipophilic components can be in the form of lipid particles and/or lipid particle crystals.

The hydrophilic phase is formed by mixing together water soluble components with water (i.e. hydrophilic portion). Examples of water soluble components include propylene glycol, glycerol, polyvinylpyrrolidone, and thickeners, e.g., xanthan gum.

The foam phase, vesicle phase and hydrophilic phases are mixed together. Preferably, an equal amount of each phase is used in the formulation.

The foam phase, vesicle phase and hydrophilic phases can be mixed together in any order. For example, the foam phase and the vesicle phase can be first mixed together, and then the resulting mixture can be mixed with the hydrophilic phase. As another example, the foam phase can be first mixed with the hydrophilic phase, and then the vesicle phase can be added.

One or more active substances can be added to the foam phase portion, the vesicle phase portion, the hydrophilic portion, or a combination of these portions.

The specific components of a formulation, and the formulation process, can be varied to obtain delivery systems which allow for different rates of the release, and degrees of penetration, of active substance(s). For example, the phase of the system in which an active substance is placed affects release and penetration rates. For instance, to enhance penetration rates of either a hydrophilic or lipophilic active substance, a major portion of the active substance is placed within the vesicle phase portion.

Another factor which affects release and penetration rates is the size of the micro-compartments. The size of the vesicles can be controlled via the formulation process. For example, during processing, as the homogenizing pressure and duration increases, the vesicle size decreases.

An additional factor which affects release and penetration rates is the type of phospholipids used in the formulation. For example, penetration can be enhanced by including a greater portion of unsaturated phospholipids within the formulation. Preferably, greater than about 90%, greater than about 95%, or greater than about 99% of the phospholipids used in the formulation are unsaturated phospholipids.

Also, phospholipids which include elevated levels of surface active single chain agents enhance penetration. Surface active single chain agents at about a level of 2% to 10% of the phospholipids are considered to be at an elevated level. Examples of surface active agents are lysophospholipids.

Examples of phospholipid formulations that enhance penetration include EPIKURON® 200SH and EPIKURON® 200, and are described above.

The concentration of free fatty acid is also an important parameter affecting penetration rates. A relatively high level of free fatty acid enhances penetration of hydrophilic active substances.

Penetration rates can also be enhanced by the addition of certain adjuvants. For example, an anionic surfactant can be added to the foam phase portion. Also, incorporation of glyceryldilaurate into the vesicle bilayers creates more flexible vesicles which can enhance penetration.

Penetration rates can also be enhanced by the addition of non-ionic adjuvants. In a preferred embodiment, the delivery systems of the present invention further comprise non-ionic adjuvants.

Unlike ionic surfactants, non-ionic adjuvants do not carry a charged species. Instead non-ionic adjuvants comprise a hydrophilic group (e.g. a short, water-soluble polymer chain). The polymers used in non-ionic adjuvants are preferably 10 to 100 units long. These adjuvants are mild on the skin even at high loadings and long-term exposure.

Non-ionic adjuvants are known in the art. Examples of non-ionic adjuvants can be found, for instance, in "Non-ionic Surfactants: Organic Chemistry," edited by Nico M. van Os, published by Marcel Dekker (1998), and "Non-ionic Surfactants: Chemical Analysis (Surfactant Science Series, Vol 19)" by John Cross, published by Marcel Dekker (Oct. 1, 1986). Some non-ionic adjuvants can be divided into classes depending on the type of hydrophilic group appearing in the adjuvant.

Two classes of non-ionic adjuvants that comprise poly (ethylene oxide) groups as their hydrophilic groups are alcohol ethoxylates and the alkylphenol ethoxylates. Examples of non-ionic adjuvants of these classes include tetraethylene glycol monododecyl ether; polyoxyethylene 23 glycol monododecyl ether, polyethylenoxide-polypropylenoxide (PEO-PPO) block-copolymers (such as the commercially available PEO-PPO-PEO triblockcopolymers, called Synperonics F108 and F127), polyoxyethylene alkylphenols; polyoxyethylene alcohols; polyoxyethylene esters of fatty acids; polyoxyethylene mercaptans; and polyoxyethylene alkylamines.

Another class of non-ionic adjuvants is the alkyl polyglycosides. In these molecules, the hydrophilic group is a sugar molecule, such as a polysaccharide, disaccharide, trisaccharide, maltose, etc. Preferably, the polyglycosides have one or two sugar groups in their chains. Examples of non-ionic adjuvants of this class include alkyl glucoside and a glucose ester.

Another class of non-ionic adjuvants is sorbitan ester surfactants. Examples of non-ionic adjuvants of this class include polysorbate 20 (i.e. polyoxyethylene (20) sorbitan monolaurate, sold as Tween 20™); polysorbate 60 (i.e. polyoxyethylene (60) sorbitan monostearate); polysorbate 80 (i.e. polyoxyethylene (20) sorbitan monooleate); and polysorbate 65 (i.e. polyoxyethylene (20) sorbitan tristearate).

The delivery systems of the invention can comprise one non-ionic adjuvant or a combination of non-ionic adjuvants.

Preferably, approximately 0.1% to approximately 15% of a delivery system of the present invention is comprised of a non-ionic adjuvant. Preferred lower boundaries of this range include approximately 0.1%, 0.2%, 0.3%, 0.4%, 0.5%, 1% and 2%. Preferred upper boundaries of this range include approximately 0.3%, 0.4%, 0.5%, 1%, 2%, 3%, 4%, 5%, 6%, 7%, 8%, 9%, 10%, 11%, 12%, 13%, 14%, and 15% of the delivery systems. Each lower boundary can be combined with each upper boundary to define a range. The lower and upper boundaries should each be taken as a separate element.

The non-ionic adjuvant can be added to the hydrophilic portion, either lipophilic portion, or combinations of these portions. Preferably the non-ionic adjuvant is added to all the portions. During the production of the hydrophilic portion or either lipophilic portion, the non-ionic adjuvant is preferably added before the mixing step.

In addition to increasing the rates of penetration of active ingredients, the inclusion of non-ionic adjuvants in the delivery systems also increases the diameter of the vesicles vis-à-vis the delivery systems without these adjuvants (while keeping the amount of active ingredient constant). The vesicle can range from approximately 0.02 µm to approximately 2.5 µm in diameter with the addition of the adjuvants. The size of the other particles are not significantly affected by the addition of the non-ionic adjuvants.

Additional factors which affect release and penetration rates include: the ratio between the different lipid components; the ratio between the foam phase, the vesicle phase and the hydrophilic phase; and the ratio between the amounts of active substances within each phase.

In one embodiment of the present invention, the lipophilic components of the delivery system form only two of the above-defined particles. That is, the formulation comprises only the gas spheres and lipid particles; or the formulation comprises only the vesicles and lipid particles.

In this embodiment, the delivery system is produced from a hydrophilic portion and a lipophilic portion. The lipophilic portion is made either into the foam phase or the vesicle phase, as described above. Preferably, the vesicle phase is produced under conditions which do not allow any gas to enter the formulation, such as in a vacuum. The foam phase or vesicle phase is mixed with the hydrophilic phase. Preferably, an equal amount of either the foam phase or vesicle phase, and the hydrophilic phase is used in the formulation.

Thus, while there have been described what are presently believed to be the preferred embodiments of the present invention, other and further embodiments, modifications, and improvements will be known to those skilled in the art, and it is intended to include all such further embodiments, modifications, and improvements and come within the true scope of the claims as set forth below.

EXAMPLES

Example 1

A General Method of Making

The phospholipid, cholesterol, palmitic acid and ceramide components are mixed together with water, and agitated at a temperature of 70-80° C. The following additional components are added: mevalonic acid lactone, 25-hydroxycholecalciferol, propylene glycol, glycerine, PVP, TEA added along with water, and sodium hydroxide. Sodium hydroxide is added to adjust viscosity and stabilize the formulation. Water is then added, and the formulation is agitated well. The formulation is then cooled down.

An active substance can be dissolved in both the lipid phase and/or the water phase, depending on the solubility and concentration of the active substance.

Example 2

Formulation of a Preferred Embodiment of the Topical Delivery System (An active ingredient is excluded from this formulation.)

| Component | Total amount |
| --- | --- |
| Water | 79.5% of formulation |
| Epikuron 200SH | 3.5% of formulation |
| Palmitic acid | 1.5% of formulation |
| Cholesterol | 1.5% of formulation |
| Mevalonic acid | 0.01% of formulation or 0.1% of formulation |
| Triethanolamine | 0.5% of formulation |
| Phenonip ® | 0.4% of formulation |
| Xanthan gum | 2.0% of formulation |
| Skinflux | 2.0% of formulation |
| 25-hydroxycholecalciferol | 0.0015% of formulation or 0.015% of formulation |
| Propylene glycol | 4.0% of formulation |
| Glycerol | 3.0% of formulation |
| Polyvinylpyrrolidone | 2.0% of formulation |

Epikuron 200SH are hydrogenated lecithins, i.e. phosphatidylcholine (PC).
"Skinflux" is a blend product obtainable from Degussa Goldschmidt which contains: Ceramide 1, 3, 6II; Phytosphingosine; Cholesterol; Sodium Lauroyl Lactylate; Carbomer; and Xanthan Gum.
Mevalonic acid lactone is a lipid precursor for cholesterol/fatty acids.
25-Hydroxycholecalciferol is a lipid precursor for ceramides
Xanthan Gum is a thickener (polysaccharide).
PHENONIP ® is a preservative and a blend of parabens.

Three fractions, a vesicle fraction, a foam fraction and a hydrophilic fraction, are first prepared separately, as described below. Each fraction weighs 3.3 kg. Then the three fractions are mixed together. The following tables show the percent amount of each component contributed by each fraction to the final formulation. Thus, for each component, the sum of the percent amounts of all the fractions is 100%.

1: Vesicle Fraction

| Component | Percent Amount in Final Formulation |
| --- | --- |
| Water | 33% of total water |
| Hydrogenated lecithins | 50% of total amount |
| Palmitic acid | 50% of total amount |
| Cholesterol | 50% of total amount |
| Mevalonic acid | 50% of total amount |
| Triethanolamine | 50% of total amount |
| Preservative (e.g., Paraben mixture) | 50% of total amount |
| Xanthan gum | 15% of total amount |
| Skinflux | 33% of total amount |
| 25-hydroxycholecalciferol | 50% of total amount |
| 5M sodium hydroxide | 1.3 ml per 1000 grams of water |

The "Percent Amount in Final Formulation" indicates the percentage of each component which is contributed by the vesicle fraction to the final formulation.

In forming the vesicle fraction, the components are mixed and heated to the temperature range of 65 to 85° C. while gently stirring. The pH is set to the range of 5.5 to 8.2 by the use of sodium hydroxide. The resulting mixture is then homogenized. Homogenization can be accomplished by, for example, a homogenizer set at a high pressure (e.g. 10,000 to 40,000 psi); or by a sonicator. The size of the vesicles is partially dependent upon how long the resulting mixture is agitated. For example, to obtain an average vesicle size of 0.140 μm, the resulting mixture is agitated for 60 minutes at about 70° C. The mixture is then allowed to cool to below 40° C.

2: Foam Fraction

| Component | Percent Amount in Final Formulation |
| --- | --- |
| Water | 33% of total water |
| Hydrogenated lecithins | 50% of total amount |
| Palmitic acid | 50% of total amount |
| Cholesterol | 50% of total amount |
| Mevalonic acid | 50% of total amount |
| Triethanol amine | 50% of total amount |
| Preservative (e.g. a paraben mixture) | 50% of total amount |
| Xanthan gum | 7.5% of total amount |
| SK-influx ® | 33% of total amount |
| 25-hydroxycholecalciferol | 50% of total amount |
| 5M sodium hydroxide | 1.3 ml per 1000 g of water |

The "Percent Amount in Final Formulation" indicates the percentage of each component which is contributed by the foam fraction to the final formulation.

In forming the foam fraction, the components are mixed and heated to the temperature range of 65 to 85° C. while stirring. The pH is set to the range of 5.5 to 8.2 by the use of sodium hydroxide. The composition is mixed vigorously for 1 minute. Mixing can be done with ULTRATURRAX® from IKA Werke, Janke & Kunkel GmbH & Co KG (Staufen, Germany). The composition is then allowed to cool to below 40° C.

3: Hydrophilic Fraction

| Component | Percent Amount in Final Formulation |
| --- | --- |
| Water | 34% of total water |
| Propylene glycol | 100% of total amount |
| Glycerol | 100% of total amount |
| Polyvinylpyrrolidone | 100% of total amount |
| Xanthan gum | 77.5% of total amount |
| Skinflux | 34% of total amount |
| 5M sodium hydroxide | 3.0 ml per 1000 g of water |

The "Percent Amount in Final Formulation" indicates the percentage of each component which is contributed by the hydrophilic fraction to the final formulation.

In forming the hydrophilic fraction, the components are mixed and heated to the temperature range of 65 to 85° C. while stirring. The pH is set to the range of 5.5 to 8.2 by use of sodium hydroxide. Once homogeneous, the composition is then allowed to cool to below 40° C.

In forming the final formulation, after all the fractions are cooled down (below 40° C.), the three fractions are mixed together in any order. For example, the foam fraction is added to the vesicle fraction and gently mixed. Then the hydrophilic fraction is added. The resulting mixture is gently blended for several minutes to obtain a homogeneous solution.

The delivery system of this example is in the form of a cream. In order to produce a delivery system in an aerosol foam form, the total amount of xanthan gum in the final formulation is reduced from 2% to about 0.3%. Additionally, an emulsifier is added, such as laureth 4. Preferably, the emulsifier makes up about 0.7% of the final formulation.

Example 3

Formulation of Example 2 with Lidocaine as an Active Ingredient

An example of a 48 kg batch of a formulation of the delivery system follows. The three fractions used to prepare this formulation each contain 16 kg.

| INCI Name | Trade Name | Supplier | CAS | Amount |
|---|---|---|---|---|
| Hydrogenated Lecithines | Epikuron 200SH | Degussa Goldschmidt | | 1.7 kg |
| Cholesterol | | Vendico | 57-88-5 | 0.8 kg |
| Palmitic acid | | Karlshamn | 57-10-3 | 0.8 kg |
| Ceramide 1, 3, 6II, Phytosphingosine, Cholesterol, Sodium Lauroyl Lactylate, Carbomer, Xanthan Gum. | Skin Flux | Degussa Goldschmidt | | 1.0 kg |
| Mevalonic acid lactone | | Sigma Aldrich | 674-26-0 | 4.8 g |
| 25-Hydroxy-cholecalciferol | | Solvay | 19356-17-3 | 0.72 kg |
| Propylene glycol | | MB-Sveda | 57-55-6 | 2.0 kg |
| Glycerin, 99.5% | | Vendico | 56-81-5 | 1.5 kg |
| Polyvinylpyrrolidone | | Apoteket | 9003-39-8 | 1.0 kg |
| Xanthan gum | | Sigma Aldrich | 11138-66-2 | 1.0 kg |
| Triethanolamine, 85% | | MB-Sveda | 102-71-6 | 0.3 kg |
| Phenonip ® | | Vendico Chemical | | 0.2 kg |
| Lidocain | USP-grade | Apoteket | | 2.4 kg |
| Purified Water | | | | Up to 48 kg |

Example 4

Measurement of Skin Barrier Restoration

In the present context enhancing skin barrier restoration can be measured by tape and/or acetone striping of stratum corneum skin lipid content before, during and after a treatment period with the present invention and other systems. Then HPLC analysis of skin lipid content of stratum corneum is conducted.

Example 5

In Vivo Model and Skin Penetration Results

Tracer amounts of the fluorescent dye NBD C6-ceramide were added to the formulation of Example 2 and to a reference (Vaseline®). The formulation and the reference were each applied to hairless mice epidermis. Skin biopsies from three mice in each experimental group were taken two hours after application for fluorescence microscopy (Zeiss Axioplan 2).

FIG. 9 is a fluorescent microscope image. This image clearly shows that the uptake of the fluorescent probe is more enhanced for the formulation of Example 2 than for the reference. Remarkably, the effect was seen as soon as two hours after application.

Example 6

Addition of Non-Ionic Adjuvants into the Formulation of Example 2

This example demonstrates how the addition of non-ionic adjuvants to the formulations of the present invention, in particular the formulation in Example 2, affects the characteristics of the formulation. This example also demonstrates a preferred distribution of active ingredients in the vesicle and foam phases.

Two different model active ingredients (model actives) were used in this example, i.e. a hydrophilic and a lipophilic model active. The lipophilic model active is acridine orange 10-nonyl bromide (AO). The hydrophilic model active is 5(6)-carboxyfluorescein (CF). The penetration of these model actives correspond to the penetration that would be obtained for typical hydrophilic and lipophilic drugs. The structures of these model actives are shown below.

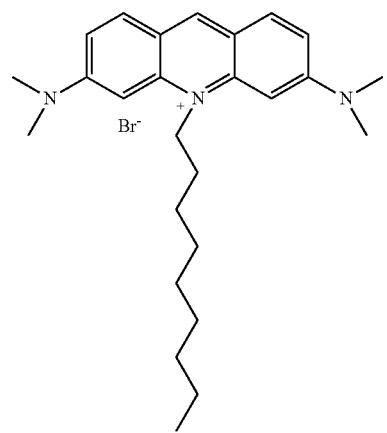

Acridine orange 10-nonyl bromide

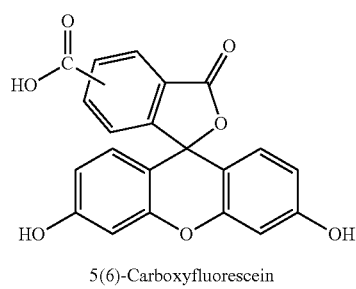

5(6)-Carboxyfluorescein

The non-ionic adjuvants used were tetraethylene glycol monododecyl ether (Brij® 30) and polyoxyethylene 23 dodecyl ether (Brij® 35), and were obtained from Sigma-Aldrich (St. Louis, Mo.). Their structures are shown below.

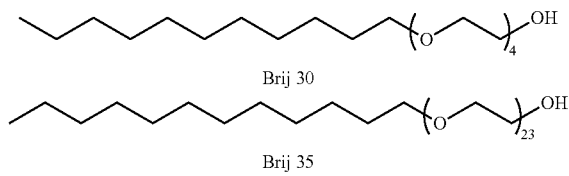

Three different variations of the formulations were studied for each model active. These formulation variations are defined as Formulation A, B and C as follows:
A) Formulation with 50% of the model active in the vesicle phase and 50% in the foam phase;
B) Formulation with all of the model active in vesicle phase; and
C) Formulation containing Brij® 30 and Brij® 35, with 50% of the model active in vesicle phase and 50% in the foam phase. The non-ionic adjuvants were added to the vesicle fraction and the foam fraction, and constituted 1.0 wt % of the total formulation.
Of the model actives, 0.028 wt % ($5.9 \cdot 10^{-4}$M) of AO was used; and 0.011 wt % ($3.0 \cdot 10^{-4}$M) of CF was used.

Characterization of Vesicle Phase

A comparison of the particle size, polydispersity index and zeta potential of the vesicles of Formulations A, B and C was conducted.

An autosizer (Malvern Zetasizer 1000HS, Malvern Instruments Ltd, Malvern, UK) was used to measure the size distribution of the vesicles. A zetasizer (Malvern Zetasizer 2000, Malvern Instruments Ltd, Malvern, UK) was used to measure the zeta potential. The zeta-potential is defined as the potential across the diffuse layer of ions surrounding the vesicles. The zeta-potential is related to the stability of the vesicles in such a way that a high magnitude of the zeta-potential implies vesicles with a higher surface charge. This higher surface charge in turn increases the repulsion between the vesicles and accordingly the stability of the formulation.

Preferably, the samples were diluted before measurements were taken. For example, before measuring the size distribution, water was used to dilute the sample. Before measuring the zeta-potential, 10 mM NaCl was used to dilute the sample.

A comparison of Formulations A, B and C with respect to the parameters of particle size, polydispersity index and zeta potential are shown in Table 1.

TABLE 1

Parameters of the Vesicle Phase for Formulations A, B and C.

| | CF | | | AO | | |
|---|---|---|---|---|---|---|
| Formulation | A | B | C | A | B | C |
| Particle diameter (nm) | 276 | 494 | 975 | 345 | 1730 | 1395 |
| Polydispersity index | 0.4 | 0.7 | 0.9 | 0.5 | 1.0 | 1.0 |
| Zeta-potential (mV) | −39 | −41 | −33 | −36 | −35 | −30 |
| pH | 7.5 | 7.4 | 7.4 | 7.3 | 7.3 | 7.3 |

As described above, the A and C formulations (CF-A, AO-A, CF-C and AO-C) have 50% of the model active in the vesicle phase and 50% in the foam phase. Only the C formulations (CF-C and AO-C) include the non-ionic adjuvants. A comparison of the A and C formulations shows that the presence of the non-ionic adjuvants significantly increase vesicle size and decreases the magnitude of zeta-potential. See Table 2.

The inclusion of the non-ionic adjuvants into the vesicle membrane results in ethylene oxide coils reaching out from the vesicle surfaces. Without wanting to be bound to a theory, it is believed that a reason for the increase in vesicle size is that a lateral pressure between ethylene oxide coils in the membrane counteracts the creation of very small vesicles. It is also believed that these coils bind water thereby increasing the mass of the vesicles and reducing their mobility which results in a decrease in the zeta-potential (Silvander et al. *Langmuir* 16:3696-3702 (2000)).

As described above, the A formulations (CF-A and AO-A) have 50% of the model active in the vesicle phase and 50% in the foam phase. The B formulations (CF-B and AO-B) have 100% of the model active in the vesicle phase. A comparison of the A and B formulations shows that the vesicle size increases when all the active is added to the vesicle phase. See Table 1.

This increase in vesicle size is much more dramatic for the formulations containing AO than those containing CF. Without wanting to be bound to a theory, it is believed that this increase results from the interaction of the lipophilic active with the membranes of the vesicles in destabilizing manner. Even though there is a small increase in the vesicle size when all the CF is added to the vesicle phase (Formulation CF-B), it is not believed that CF interacts with the membranes to any large extent. Instead, the difference is likely due to a normal variance in the preparation process.

Characterization of the Foam Phase

The foam phase was investigated by means of light microscopy. As can be seen in FIG. 5, the distribution of the gas spheres of the foam phase is broad. No differences in the parameters of particle size, polydispersity index and zeta potential were found between Formulations A, B and C for each model active. The phase volume of air directly after production was estimated to 7% directly after production (Master size measurements) and was the same after five days storage at room temperature.

Stability of the Formulations

A change in color of the formulations would indicate oxidation of phospholipids or physical separation. No color change was observed even after 12 months storage both at about 25° C. and at about 40° C. It is believed that the physical stability is ensured due to the negative potential of the small particles together with the gel-like character of the total formulation.

Example 7

Skin Penetration Model

Diffusion Cell

Pig skin was chosen to investigate skin penetration since its stratum corneum structure resembles human stratum corneum more than does mouse skin (Bouwstra et al. *J. Lipid Res.* 36(4): 685-95 (1995)).

Ears of seven to eight month old pigham pigs were obtained from Swedish Meat (Uppsala, Sweden) approximately two hours after slaughter and used the same day. Patches of ear skin were removed with a scalpel. The appropriate thickness (640 μm) was obtained by use of a manual dermatome (Padgett Dermatome, Padgett Instruments Inc., Kansas City). The skin was mounted on diffusion cells of a skin permeation system (Laboratory Glass Apparatus Inc., CA, USA). The receiver capacity of the system was 3 ml. The skin was mounted with the stratum corneum facing upwards. The surface area of the skin patches was 0.67 cm².

An amount of 100 µl of each formulation being tested was applied to the skin and carefully spread to cover the entire surface area. The formulations tested were Formulations AO-A, AO-B, AO-C, CF-A, CF-B, CF-C from Example 6, and two reference formulations. For the AO formulations, Vaseline® containing 0.028 wt % AO was used as a reference. For the CF formulations, xanthan gum gel containing 0.011 wt % CF was used as a reference. Because of the high viscosity of the formulations, the exact amount was determined by weighing after application. For each formulation, three experiments were performed using skin patches from different pigs. The receiver compartment was continuously rinsed with 25 mM HEPES buffer containing 133 mM NaCl (isotonic conditions). The pH of the buffer was set to 7.4 by addition of 1 M NaOH. Before use, the buffer was placed in an ultrasound bath for a few minutes to remove air bubbles. When connecting the buffer solution to the receiver compartment, care was exercised to ensure that no air bubbles appeared on the dermal side of the skin or elsewhere in the receiver compartment. The receiver solution was continuously stirred using a small magnet and the temperature was maintained at 37° C. throughout the experiment by coupling a water bath (HETO, Denmark) to the cells. The experiments were carried out for 24 hours under non-occluded conditions and fractions were collected from the receiver. The flow rate of the receiver solution was set to 1-2 ml/h and fractions were collected every 90 minutes throughout the experiment. After 24 hours, the flow through the receiver compartment was stopped and the donor compartment was rinsed. The first rinsing was performed with 10 ml HEPES buffer followed by two rinses of 10 ml methanol. In cases where the formulation contained 10-nonyl bromide acridine orange, the first rinsing step was excluded since the probe is not soluble in HEPES buffer.

Tape Stripping Procedure

The skin patches were placed on a board. The remaining dried formulations were removed and placed in HEPES buffer. Then the skin patches were stripped. The stripping was carried out using adhesive tape (Scotch magic tape, 3M) by covering the area of the skin that had been in contact with the formulation with a piece of tape, 1.9 cm wide and 4 cm long. Fifteen strippings were performed to ensure that the stratum corneum was removed (Plessis et al. Int. J. Pharm. 103:R1-R5 (1994)). The first two tape strips (Strips 1 and 2) were used to get rid of excess formulation on the skin. Strips 1 and 2 were used to get rid of excess formulation on the skin. Strips 3-5 represent the upper stratum corneum. Strips 6-10 represent the middle stratum corneum. Strips 11-15 represent the lower stratum corneum. The strips were placed into 5 ml HEPES buffer or ml methanol depending on the solubility of the probe. The remaining skin was placed in HEPES buffer for at least 48 hours and after that in methanol for at least 24 hours. These solutions are referred to as the extraction fractions. In cases where the formulation contained acridine orange 10-nonyl bromide, the skin was only placed in methanol for at least 24 hours.

In summary, after stopping the flow though the receiver compartment, the skin was rinsed and tape stripped giving rise to the following fractions:
1. 10 ml HEPES buffer
2. 10 ml methanol
3. 10 ml methanol
4. Remaining dried formulation
5. Tape strips 1-2, excess formulation
6. Tape strips 3-5, surface stratum corneum
7. Tape strips 6-10, middle stratum corneum
8. Tape strips 11-15, deeper stratum corneum
9. Extraction fractions Fraction Analysis The collected fractions were analysed by use of a spectrofluorimeter (FluoroMax-2, Instruments S. A., Inc.). The wave lengths found were 490 nm (excitation) and 513 nm (emission) for CF in HEPES, and 490 mm (excitation) and 517 nm (emission) for AO in methanol. Special care was taken in order for the fractions containing CF to be in a linear concentration to intensity region (Weinstein et al. Liposome Technology Gregoriadis, G., ed. Vol. 3, pp. 183, CRC Press, Boca Raton).

Example 8

Skin Penetration Results of the Formulations of Example 7

This example shows the performance results of the penetration of Formulations AO-A, AO-B, AO-C, CF-A, CF-B, CF-C, and the references Vaseline® and xanthan gum gel, as tested by the model described in Example 7. These results demonstrate that the non-ionic adjuvants work well both for hydrophilic and lipophilic actives.

Results for the CF Formulations

The penetration behaviours of the hydrophilic active for the different CF formulations (CF-A, CF-B, CF-C), and for the reference xanthan gum gel formulation, are shown in FIG. 6.

The amount detected in stratum corneum was similar for CF-A, CF-B and the reference xanthan gum gel. A larger amount of CF was found in the stratum corneum for the CF-C formulation, thus demonstrating that the adjuvants increase penetration.

Concerning the total amount detected in skin, both the CF-B and CF-C formulations penetrate better than does the reference xanthan gum gel. These results show that it is beneficial to distribute more of a hydrophilic active in the vesicle phase when a larger uptake is desired; and that it is beneficial to add non-ionic adjuvants to a formulation when a larger uptake is desired.

These results also show that in addition to the size of the vesicles influencing penetration, there is an effect of the vesicle carrier per se. That is, although the vesicles are smaller in the CF-B formulation vis-à-vis the CF-C formulation, the total amount of the active ingredient detected in the skin is similar. Without wanting to be bound by a mechanism, it is believed that the effect is probably due to an ability of small vesicles to function as carriers down to a lower depth of the skin.

The largest amount of actives found in the receiver was for the reference xanthan gum gel formulation. That is, an active in the gel is more easily transferred to the receiver than is an active incorporated into the lipid matrices of the formulations of the present invention. Thus an active incorporated into the xanthan gum gel is not retained. Without wanting to be bound by a mechanism, it is believed that this occurs because the amount of free water in the xanthan gum is larger than in the other formulations. Water is known to work as a penetration enhancer (Willams et al, *Crit. Rev. Ther. Drug Carrier Syst.* 9(3-4):305-53 (1992)). Moreover, the conditions with a large amount of free water in a gel layer of non-negligible height is close to occluded conditions. Such conditions have been reported beneficial for uptake of drugs (Honeywell et al. *J Controlled Release* 90:243-55 (2003), Bodde et al. *Crit. Rev. Ther. Drug Carrier Syst* 61:87-115). However, the slow release from the formulations of the present invention to the receiver indicate a slow release mechanism that is beneficial for many topical treatments since systemic toxicity is more easily avoided.

Results for the AO Formulations

The penetration behaviours of the lipophilic active for the different AO formulations (AO-A, AO-B, AO-C) and the reference Vaseline®, are shown in Table 2 and FIG. 7.

The amount of AO in the total skin is highest for the formulation containing the non-ionic adjuvants, i.e. AO-C. The incorporation of all of the AO into the vesicle phase (AO-B) did not have any beneficial effect on the total skin penetration. Without wanting to be bound to a mechanism, it is believed that this is due in part to that the homogenization was less efficient with all of the AO placed into the vesicle phase. This mechanism is supported by the observation that the vesicle size distribution was large. (See Table 2).

The deeper layers of the stratum corneum contain much less AO when Vaseline® is used than when the other formulations are used. See Table 2 and FIG. 8. Notably, the formulation containing the adjuvants (AO-C) delivered more than twice the total amount of AO to the deeper layer of the stratum corneum than that delivered by the reference. This is a dramatic improvement. Also, when evaluating the deeper parts of the skin (i.e. below SC), delivery is increased by over four times.

TABLE 2

Penetration of AO and Vaseline into the Stratum Corneum

|  | AO-A | AO-B | AO-C | Vaseline ® |
|---|---|---|---|---|
| Surface SC | 0.56 | 0.93 | 1.03 | 1.25 |
| Middle SC | 0.70 | 0.55 | 0.68 | 0.45 |
| Deeper SC | 0.44 | 0.34 | 0.40 | 0.17 |
| Total SC | 1.70 | 1.82 | 2.11 | 1.87 |

Note that no amount of AO could be detected in the receiver since its water solubility is low.

Example 9

Variation of the Vesicle Fraction of the Formulation

The object of this example was to evaluate how the physical properties of the vesicle fraction change when its formulation is varied. The vesicle fraction of the formulation of Example 2 was varied with respect to pH, amount of cholesterol, type of phospholipids and addition of surface active agents. The parameters which were varied are presented in Table 3. In particular, fraction L1 is the standard formulation of Example 2. Fraction L3 is the same as fraction L1 except that the Epikuron 200SH phospholipid mixture is replaced with Epikuron 170. Fraction L7 is the same as fraction L1 except that Epikuron 200SH is replaced with Epikuron 200. Fractions L8, L9 and L10 are the same as fraction L7 except that the amount of cholesterol is varied. Fraction L11 is the same as fraction L1 except that surface active agents are included (i.e. Brij 30 and Brij 35). Fractions L2, L5 and L6 are the same as fraction L1 except that the pH is varied. Fraction L4 is the same as fraction L1 except that the amount of cholesterol is reduced.

All fractions were prepared as described in Example 2 except for the varied characteristic. Additionally, unlike in Example 2, the sonication time was prolonged up to 120 minutes in order to study the effect of this on the vesicle properties. Samples were collected after 30, 60 and 120 minutes of sonication for most of the fractions.

TABLE 3

Variation of the composition of the vesicle fraction.

| Fraction Name | Varied Characteristic |
|---|---|
| L1 | Example 2 Formulation (i.e. no variation) |
| L2 | 2.0 ml 5M NaOH per 1000 g water |
| L3 | Epikuron 170 |
| L4 | 17% cholesterol (of total amount) |
| L5 | 4.0 ml 5M NaOH per 1000 g water |
| L6 | 7.0 ml 5M NaOH per 1000 g water |
| L7 | Epikuron 200, 50% cholesterol |
| L8 | Epikuron 200, 20% cholesterol |
| L9 | Epikuron 200, without cholesterol |
| L10 | Epikuron 200, 10% cholesterol |
| L11 | Addition of 0.5% Brij 30 and 0.5% Brij 35 |

The particle sizes in the vesicle fractions after different sonication times are summarized in Table 4. The diameter given is the Z-average that has been calculated directly from Stoke-Einsteins equation. PI is the polydispersity index. For L3-L6, the particle size was only studied after 30 and 120 minutes sonication.

TABLE 4

Vesicle size and polydispersity index (PI) after 30, 60 and 120 min sonication.

| Fraction | Zeta Potential (mv) | 30 min Diameter (nm) | 30 min PI | 60 min Diameter (nm) | 60 min PI | 120 min Diameter (nm) | 120 min PI |
|---|---|---|---|---|---|---|---|
| L1 | −44 ± 1.6 | 130 | 0.43 | 130 | 0.42 | 131 | 0.42 |
| L2 | −50 ± 0.9 | 140 | 0.34 | 130 | 0.36 | 140 | 0.36 |
| L3 | −47 ± 2.9 | 200 | 0.27 | — | — | 370 | 0.51 |
| L4 | −41 ± 0.8 | 1100 | 1.00 | — | — | 2300 | 1.00 |
| L5 | −50 ± 3.6 | 170 | 0.23 | — | — | 190 | 0.23 |
| L6 | −38 ± 1.2 | 210 | 0.27 | — | — | 190 | 0.24 |
| L7 | −51 ± 2.9 | 860 | 1.00 | — | 1.00 | 130 | 0.45 |
| L8 | −29 ± 3.6 | 530 | 0.66 | 170 | 0.28 | 180 | 0.39 |
| L9 | −31 ± 4.7 | 150 | 0.50 | — | 1.00 | 130 | 0.78 |
| L10 | −32 ± 3.8 | 160 | 0.62 | 170 | 0.56 | 220 | 0.58 |
| L11 | −30 ± 0.4 | 780 | 1.00 | 1600 | 1.00 | 1500 | 1.00 |

The choice of phospholipid is shown to be important for the properties of the vesicle fraction. Epikuron 200SH, 200 and 170 all are mixtures of phospholipids but differ in the saturation and chain length of the phospholipids and also in their amounts of soya phosphatidylcholines (PC).

From the results presented in Table 4, it is clear that use of Epikuron 170 (fraction L3) gives rise to larger vesicles vis-à-vis Epikuron 200SH (fraction L1). The phospholipids of Epikuron 170 are less saturated than the phospholipids in Epikuron 200SH.

The phospholipids in Epikuron 200 (fraction L7) are also less saturated than Epikuron 200SH. However, the difference in vesicle size between fraction L1 (Epikuron 200SH) and fraction L7 (Epikuron 200) is small after 120 minutes sonication.

Thus, after 120 minutes of sonication, when compared to the standard formulation containing Epikuron 200SH, Epikuron 170 yields larger vesicles while Epikuron 200 does not. Without wanting to be bound by a mechanism, it is believed that this result is because Epikuron 170 contains approximately 8% phosphatidylethanolamine (PE), while Epikuron 200 does not. PE has much smaller head groups than PC and so forms inverted structures that can make the formation of membranes more difficult.

The amount of cholesterol also influences the vesicle size, and particle stability. For example, when the amount of cholesterol in the formulation is lowered to 17% (fraction L4) vis-à-vis the standard formulation wherein cholesterol is 50% (fraction L1), the vesicle size is dramatically increased, and the zeta potential is decreased.

Additionally, comparison between fractions L7, L8, L9 and L10 also indicates that the amount of cholesterol affects the stability of the vesicles in such a way that a higher amounts of cholesterol give rise to more stable vesicles (higher magnitude of the zeta potential). Fractions L7, L8, L9 and L10 contain 50%, 20%, 0% and 10% cholesterol, respectively. Fractions L8, L9 and L10 have much lower zeta potentials than L7. additionally, the level of cholesterol is also seen to affect the stability of vesicles more when saturated phospholipids are used vis-à-vis when unsaturated phospholipids are used.

For fractions L7 and L8, the sonication time is of importance to obtain vesicles of the desirable size and size distribution. There is a distinct decrease in vesicle size between 30 and 120 minutes of sonication for these fractions. However, for the other fractions sonication for more than 30 minutes seem to be unnecessary since there is no particular change in vesicle size with increased time of sonication. In some cases, for example fraction L4, it even appears that the particle size is increased with increased sonication time. Without wanting to be bound by a mechanism, a possible explanation for this increase is that oxidation occurs in the sample during the sonication.

The addition of the surfactants Brij 30 and Brij 35 (fraction 11) increases the vesicle size considerably. Without wanting to be bound by a mechanism, an explanation for this is that the addition of surfactants increases the fluidity of the vesicle membranes. It is also possible that additional surface active agents decrease the stability of the vesicles by increasing the steric repulsions between the head groups on the inside of the vesicles. What is usually an advantage for the outer part of the membrane has in general a negative effect on the inside of the vesicles.

I claim:

1. A method of delivering an active substance through the stratum corneum, the method comprising applying to skin a delivery composition comprising:
    an aqueous carrier, wherein water comprises 65% or more of the delivery composition by weight;
    a lipid component suspended in the aqueous carrier comprising lipids consisting essentially of
        (a) fatty acid, which comprises 0.5-10% by weight of the delivery composition, which fatty acid is fatty acid of 10 to 24 carbons,
        (b) cholesterol, which comprises 0.5-7% by weight of the delivery composition, and
        (c) phospholipid and/or ceramide which component is 0.5-20% by weight of the delivery composition, wherein the phospholipid and/or ceramide component comprises 5% or more by weight phospholipid, and wherein the weight ratio of phospholipid/ceramide to cholesterol is 2:1 to 5.9:1, and
        (d) optionally, skin lipid precursors, wherein a combination of said lipids comprises 2 to 20% by weight of the delivery composition;
    said lipid component comprises:
        (i) a lipid particle component comprising particles formed from said lipids, said particles being surrounded by a lipid monolayer, the particles ranging from approximately 1 µm to approximately 150 µm in diameter, and
        (ii) a vesicle component comprising vesicles of formed from said lipids enclosed by a lipid bilayer, the vesicles ranging from approximately 0.02 µm to approximately 0.5 µm in diameter; and
    a bioactive agent suitable for delivery to or through skin.

2. The method of claim 1, wherein the phospholipid and/or ceramide component comprises 10% or more by weight phospholipid.

3. The method of claim 1, wherein the phospholipid and/or ceramide component comprises 15% or more by weight phospholipid.

4. The method of claim 1, wherein the phospholipid and/or ceramide component comprises 20% or more by weight phospholipid.

5. The method of claim 1, wherein a predominant portion of the fatty acid component is C16 or C18 fatty acid.

6. The method of claim 1, wherein the weight ratio of phospholipid/ceramide to fatty acid is 2:1.5 to 2.95:0.5.

7. The method of claim 6, wherein phospholipid and/or ceramide component comprises 20% or more by weight phospholipid.

8. The method of claim 6, wherein the combination of said lipids comprises 3 to 18% by weight of the delivery composition.

9. The method of claim 6, wherein the combination of said lipids comprises 4 to 16% by weight of the delivery composition.

10. The method of claim 6, wherein the combination of said lipids comprises 5 to 13% by weight of the delivery composition.

11. The method of claim 6, wherein a predominant portion of the fatty acid component is C16 or C18 fatty acid.

12. The method of claim 6, wherein the bioactive agent is a peptide, protein, sunscreen, tanning agent, skin anti-wrinkling agent, anti-dandruff agent, anti-acne agent, hair growth stimulant, hormone, nicotine, interferon, pain killer, vitamin, antifungal, anti-acne, anti-louse agent, anti-skin cancer agent or a substance to treat eczema, dry skin, itchy skin, hair loss, psoriasis or skin lesions.

13. The method of claim 6, wherein the bioactive agent is a steroid hormone.

14. The method of claim 6, wherein the lipid component comprises 25-hydroxycholecalciferol, mevalonic acid, mevalonic acid lactone or mixtures thereof as skin lipid precursor.

15. The method of claim 1, wherein the combination of said lipids comprises 3 to 18% by weight of the delivery composition.

16. The method of claim 1, wherein the combination of said lipids comprises 4 to 16% by weight of the delivery composition.

17. The method of claim 1, wherein the combination of said lipids comprises 5 to 13% by weight of the delivery composition.

18. The method of claim 1, wherein the bioactive agent is a peptide, protein, sunscreen, tanning agent, skin anti-wrinkling agent, anti-dandruff agent, anti-acne agent, hair growth stimulant, hormone, nicotine, interferon, pain killer, vitamin, antifungal, anti-acne, anti-louse agent, anti-skin cancer agent or a substance to treat eczema, dry skin, itchy skin, hair loss, psoriasis or skin lesions.

19. The method of claim 1, wherein the bioactive agent is a steroid hormone.

20. The method of claim 1, wherein the lipid component comprises 25-hydroxycholecalciferol, mevalonic acid, mevalonic acid lactone or mixtures thereof as skin lipid precursor.

21. The method of claim 1, wherein water comprises 70% or more of the delivery composition by weight.

22. The method of claim 21, wherein the phospholipid and/or ceramide component comprises 10% or more by weight phospholipid.

23. The method of claim 21, wherein the phospholipid and/or ceramide component comprises 15% or more by weight phospholipid.

24. The method of claim 21, wherein the phospholipid and/or ceramide component comprises 20% or more by weight phospholipid.

25. The method of claim 21, wherein a predominant portion of the fatty acid component is C16 or C18 fatty acid.

26. The method of claim 21, wherein the weight ratio of phospholipid/ceramide to fatty acid is 2:1.5 to 2.95:0.5.

27. The method of claim 26, wherein the phospholipid and/or ceramide component comprises 10% or more by weight phospholipid.

28. The method of claim 26, wherein the phospholipid and/or ceramide component comprises 15% or more by weight phospholipid.

29. The method of claim 26, wherein the phospholipid and/or ceramide component comprises 20% or more by weight phospholipid.

30. The method of claim 26, wherein the combination of said lipids comprises 3 to 18% by weight of the delivery composition.

31. The method of claim 26, wherein the combination of said lipids comprises 4 to 16% by weight of the delivery composition.

32. The method of claim 26, wherein the combination of said lipids comprises 5 to 13% by weight of the delivery composition.

33. The method of claim 26, wherein a predominant portion of the fatty acid component is C16 or C18 fatty acid.

34. The method of claim 26, wherein the bioactive agent is a peptide, protein, sunscreen, tanning agent, skin anti-wrinkling agent, anti-dandruff agent, anti-acne agent, hair growth stimulant, hormone, nicotine, interferon, pain killer, vitamin, antifungal, anti-acne, anti-louse agent, anti-skin cancer agent or a substance to treat eczema, dry skin, itchy skin, hair loss, psoriasis or skin lesions.

35. The method of claim 26, wherein the bioactive agent is a steroid hormone.

36. The method of claim 26, wherein the lipid component comprises 25-hydroxycholecalciferol, mevalonic acid, mevalonic acid lactone or mixtures thereof as skin lipid precursor.

37. The method of claim 21, wherein the combination of said lipids comprises 3 to 18% by weight of the delivery composition.

38. The method of claim 21, wherein the combination of said lipids comprises 4 to 16% by weight of the delivery composition.

39. The method of claim 21, wherein the combination of said lipids comprises 5 to 13% by weight of the delivery composition.

40. The method of claim 21, wherein the bioactive agent is a peptide, protein, sunscreen, tanning agent, skin anti-wrinkling agent, anti-dandruff agent, anti-acne agent, hair growth stimulant, hormone, nicotine, interferon, pain killer, vitamin, antifungal, anti-acne, anti-louse agent, anti-skin cancer agent or a substance to treat eczema, dry skin, itchy skin, hair loss, psoriasis or skin lesions.

41. The method of claim 21, wherein the bioactive agent is a steroid hormone.

42. The method of claim 21, wherein the lipid component comprises 25-hydroxycholecalciferol, mevalonic acid, mevalonic acid lactone or mixtures thereof as skin lipid precursor.

43. The method of claim 1, wherein the composition is delivered to the skin as a foam and water comprises 75% or more of the delivery composition by weight.

44. The method of claim 43, wherein the phospholipid and/or ceramide component comprises 10% or more by weight phospholipid.

45. The method of claim 43, wherein the phospholipid and/or ceramide component comprises 15% or more by weight phospholipid.

46. The method of claim 43, wherein the phospholipid and/or ceramide component comprises 20% or more by weight phospholipid.

47. The method of claim 43, wherein a predominant portion of the fatty acid component is C16 or C18 fatty acid.

48. The method of claim 43, wherein the weight ratio of phospholipid/ceramide to fatty acid is 2:1.5 to 2.95:0.5.

49. The method of claim 48, wherein the phospholipid and/or ceramide component comprises 10% or more by weight phospholipid.

50. The method of claim 48, wherein the phospholipid and/or ceramide component comprises 15% or more by weight phospholipid.

51. The method of claim 48, wherein the phospholipid and/or ceramide component comprises 20% or more by weight phospholipid.

52. The method of claim 48, wherein the combination of said lipids comprises 3 to 18% by weight of the delivery composition.

53. The method of claim 48, wherein the combination of said lipids comprises 4 to 16% by weight of the delivery composition.

54. The method of claim 48, wherein the combination of said lipids comprises 5 to 13% by weight of the delivery composition.

55. The method of claim 48, wherein a predominant portion of the fatty acid component is C16 or C18 fatty acid.

56. The method of claim 48, wherein the bioactive agent is a peptide, protein, sunscreen, tanning agent, skin anti-wrinkling agent, anti-dandruff agent, anti-acne agent, hair growth stimulant, hormone, nicotine, interferon, pain killer, vitamin, antifungal, anti-acne, anti-louse agent, anti-skin cancer agent or a substance to treat eczema, dry skin, itchy skin, hair loss, psoriasis or skin lesions.

57. The method of claim 48, wherein the bioactive agent is a steroid hormone.

58. The method of claim 48, wherein the lipid component comprises 25-hydroxycholecalciferol, mevalonic acid, mevalonic acid lactone or mixtures thereof as skin lipid precursor.

59. The method of claim 43, wherein the combination of said lipids comprises 3 to 18% by weight of the delivery composition.

60. The method of claim 43, wherein the combination of said lipids comprises 4 to 16% by weight of the delivery composition.

61. The method of claim 43, wherein the combination of said lipids comprises 5 to 13% by weight of the delivery composition.

62. The method of claim 43, wherein the bioactive agent is a peptide, protein, sunscreen, tanning agent, skin anti-wrinkling agent, anti-dandruff agent, anti-acne agent, hair growth stimulant, hormones, nicotine, interferon, pain killer, vitamin, antifungal, anti-acne, anti-louse agent, anti-skin cancer agent or a substance to treat eczema, dry skin, itchy skin, hair loss, psoriasis or skin lesions.

63. The method of claim 43, wherein the bioactive agent is a steroid hormone.

64. The method of claim 43, wherein the lipid component comprises 25-hydroxycholecalciferol, mevalonic acid, mevalonic acid lactone or mixtures thereof as skin lipid precursor.

65. The method according to claim 1, wherein the delivery composition comprises: fatty acid at between 0.5-10%; the cholesterol at between 0.5-10%; the lipid precursors at between 0.000001-10%; and the ceramide/phospholipid portion at between 0.005-20%.

66. The method according to claim 1, wherein the delivery composition comprises: fatty acid comprising ten to twenty-four carbon atoms.

67. The method according to claim 1, wherein the water content in the delivery composition exceeds 79%.

68. The method according to claim 1, wherein the water content in the delivery composition exceeds 90%.

69. The method according to claim 1, wherein the delivery composition comprises a combination of:
Fatty Acid 0.5-10%
Phospholipid 0.5-10%
Cholesterol 0.5-7%
Lipid precursor 0.000001-10%
Ceramide 0.005%-7%.

70. The method according to claim 69, wherein the lipid precursor in the delivery composition is mevalonic acid.

71. The method according to claim 69, wherein the delivery composition further comprises
Glycerine 0-5%
Propylene glycol 0-48%
PVP (M weight 40.000) 0-5%
triethanolamine (TEA) 0-3%.

72. The method according to claim 69, wherein the delivery composition further comprises
25-Hydroxycholecalciferol 0.015%
Acylceramides 0.025%.

73. The method according to claim 69, wherein the lipid precursor comprises 0.01% of Mevalonic acid, 0.0015% 25-Hydroxycholecalciferol, or a combination of Mevalonic acid, and 25-Hydroxycholecalciferol.

* * * * *